(12) United States Patent
Prather et al.

(10) Patent No.: US 10,405,526 B2
(45) Date of Patent: Sep. 10, 2019

(54) PORCINE REPRODUCTIVE AND RESPIRATORY SYNDROME VIRUS RESISTANT ANIMALS

(71) Applicant: The Curators of the University of Missouri, Columbia, MO (US)

(72) Inventors: Randall S. Prather, Rocheport, MO (US); Kevin D. Wells, Columbia, MO (US); Kristin M. Whitworth, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 16/111,631

(22) Filed: Aug. 24, 2018

(65) Prior Publication Data

US 2018/0368374 A1 Dec. 27, 2018

Related U.S. Application Data

(63) Continuation of application No. 15/783,417, filed on Oct. 13, 2017, now Pat. No. 10,080,353, which is a continuation of application No. 14/117,943, filed as application No. PCT/US2012/038193 on May 16, 2012, now Pat. No. 9,820,475.

(60) Provisional application No. 61/519,076, filed on May 16, 2011.

(51) Int. Cl.
*A01K 67/027* (2006.01)
*C12N 15/85* (2006.01)
*C07K 14/705* (2006.01)

(52) U.S. Cl.
CPC ...... *A01K 67/0276* (2013.01); *C12N 15/8509* (2013.01); *A01K 2217/075* (2013.01); *A01K 2217/15* (2013.01); *A01K 2227/108* (2013.01); *A01K 2267/02* (2013.01); *C07K 14/7056* (2013.01); *C07K 14/70596* (2013.01)

(58) Field of Classification Search
CPC .................................................. A01K 67/0276
See application file for complete search history.

(56) References Cited

U.S. PATENT DOCUMENTS

| 5,945,577 | A | 8/1999 | Stice et al. | |
|---|---|---|---|---|
| 6,211,429 | B1 | 4/2001 | Machaty et al. | |
| 9,820,475 | B2 * | 11/2017 | Prather | A01K 67/0276 |
| 10,080,353 | B2 * | 9/2018 | Prather | A01K 67/0276 |
| 2005/0120400 | A1 | 6/2005 | Day et al. | |
| 2005/0260176 | A1 | 11/2005 | Ayares et al. | |
| 2009/0104147 | A1 | 4/2009 | Delputte et al. | |
| 2010/0158947 | A1 | 6/2010 | Delputte et al. | |
| 2011/0016543 | A1 | 1/2011 | Weinstein et al. | |
| 2011/0016546 | A1 * | 1/2011 | Bedell | A01K 67/0275 800/17 |
| 2011/0038841 | A1 | 2/2011 | Ayares | |
| 2012/0180141 | A1 | 7/2012 | Welsh et al. | |

FOREIGN PATENT DOCUMENTS

| JP | 09-298981 A | 11/1997 |
|---|---|---|
| WO | 96/07732 A1 | 3/1996 |
| WO | 97/07668 A1 | 3/1997 |
| WO | 97/07669 A1 | 3/1997 |
| WO | 2005/104835 A2 | 11/2005 |
| WO | 2008/106986 A1 | 11/2008 |

OTHER PUBLICATIONS

Albina, E., et al., "Immune Response and Persistance of the Porcine Reproductive and Respiratory Syndrome Virus In Infected Pigs and Farm Units," The Veterinary Record, May 1994, pp. 567-573, vol. 134, No. 22.

Allende, R, et al., "Porcine Reproductive and Respiratory Syndrome Virus: Description of Persistance in Individual Pigs Upon Experimental Infection," Journal of Virology, Nov. 2000, pp. 10834-10837, vol. 74, No. 22.

American Society for Cell Biology, "Small Details Between "In Vivo" and "In Vitro" Studies Make for Big Differences," Science Daily, Dec. 13, 2010, <www.sciencedaily.com/releases/2010/12/101213101804.htm>, 3 pages.

Andreyev, V. G., et al., "Genetic Variation and Phylogenetic Relationships of 22 Porcine Reproductive and Respiratory Syndrome Virus (Prrsv) Field Strains Based on Sequence Analysis of Open Reading Frame 5." Archives of Virology, 1997, pp. 993-1001, vol. 142, No. 5.

ATCC, "293T (ATCC(R) CRL-3216(TM))," accessed from <https://www.atcc.org/Products/All/CRL-3216.aspx> on Sep. 29, 2016, 2 pages.

Benfield, D.A., et al., "Characterization of Swine Infertility and Respiratory Syndrome (SIRS) Virus (Isolate ATCC VR-2332)," Journal of Veterinary Diagnostic Investigation, 1992, pp. 127-133, vol. 4.

Benfield, D. A., et al., "Pathogenesis and Persistence of PRRS," Proceedings, Allen D. Leman Swine conference, 1998, pp. 169-171.

Berg, H., "500-Biological Implications of Electric Field Effects, Part V. Fusion of Blastomeres and Blastocysts of Mouse Embryos," Bioelectrochemistry and Bioenergetics, 1982, pp. 223-228, vol. 9.

Burlak, C., et al., "Identification of Human Preformed Antibody Targets in GTKO Pigs," Xenotransplantation, Mar.-Apr. 2012, pp. 92-101, vol. 19, No. 2.

Christopher-Hennings, J., et al., "Persistence of Porcine Reproductive and Respiratory Syndrome Virus in Serum and Semen of Adult Boars," Journal of Veterinary Diagnostic Investigation, 1995, pp. 456-464, vol. 7, No. 4.

(Continued)

*Primary Examiner* — Scott Long
(74) *Attorney, Agent, or Firm* — Stinson LLP

(57) ABSTRACT

The present invention generally relates to genetically modified swine wherein at least one allele of a SIGLEC1 gene has been inactivated and/or at least one allele of a CD163 gene has been inactivated. Genetically modified swine having both alleles of the SIGLEC1 gene and/or both alleles CD163 gene inactivated are resistant to porcine reproductive and respiratory syndrome virus (PRRSV). Methods for producing such transgenic swine are also provided.

19 Claims, 6 Drawing Sheets

Specification includes a Sequence Listing.

(56) References Cited

OTHER PUBLICATIONS

Christopher-Hennings, J., et al., "Effects of a Modified-Live Virus Vaccine Against Porcine Reproductive and Respiratory Syndrome in Boars," American Journal of Veterinary Research, 1997, pp. 40-45, vol. 58, No. 1.

Cooper, D. K. C., "Modifying the Sugar Icing on the Transplantation Cake," Glycobiology, Jun. 2016, pp. 571-581, vol. 26, No. 6.

Crocker, P. R., et al., "Properties and Distribution of a Lectin-Like Hemagglutinin Differentially Expressed by Murine Stromal Tissue Macrophages," The Journal of Experimental Medicine, 1986, pp. 1862-1875, vol. 164, No. 3.

Crocker, P. R., et al., "Molecular Analysis of Sialoside Binding to Sialoadhesin by NMR and Site-Directed Mutagenesis," Biochemical Journal, 1999, pp. 355-361, vol. 341(Part 2).

Das, P. B., et al., The Minor Envelope Glycoproteins GP2a and GP4 of Porcine Reproductive and Respiratory Syndrome Virus Interact with the Receptor CD163, Journal of Virology, 2010, pp. 1731-1740, vol. 84, No. 4.

Dee, S. A, et al., "Elimination of Porcine Reproductive and Respiratory Syndrome Virus Using a Test and Removal Process," The Veterinary Record, 1998, pp. 474-476, vol. 143, No. 17.

Delputte, P. L., et al., "Effect of Virus-Specific Antibodies on Attachment, Internalization and Infection of Porcine Reproductive and Respiratory Syndrome Virus in Primary Macrophages," Veterinary Immunology and Immunopathology, 2004, pp. 179-188, vol. 102, No. 3.

Delputte, P. L., et al., "Porcine Arterivirus Infection of Alveolar Macrophages is Mediated by Sialic Acid on the Virus," Journal of Virology, 2004, pp. 8094-8101, vol. 78, No. 15.

Delputte, P. L., et al., "Porcine Arterivirus Attachment to the Macrophage-Specific Receptor Sialoadhesin is Dependent on the Sialic Acid-Binding Activity of the N-Terminal Immunoglobulin Domain of Sialoadhesin," Journal of Virology, 2007, pp. 9546-9550, vol. 81, No. 17.

Delputte, P. L., et aL, "Porcine Sialoadhesin (CD169/Siglec-1) is an Endocytic Receptor that Allows Targeted Delivery of Toxins and Antigens to Macrophages," PLoS One, Feb. 2011, e16827, pp. 1-12, vol. 6, No. 2.

Fisher, D., et aL, "Membrane Fusion by Viruses and Chemical Agents," Techniques in Cellular Physiology, 1981, pp. 1-36, vol. P115.

Fridman, A. L., et al., "Critical Pathways in Cellular Senescence and Immortalization Revealed by Gene Expression Profiling," Oncogene, 2008, pp. 5975-5987, vol. 27, No. 46.

Galili, U., "Xenotransplantation and ABO Incompatible Transplantation: The Similarities They Share," Transfusion and Apheresis Science, 2006, pp. 45-58, vol. 35, No. 1.

Gerrits, R. J., et al., "Perspectives for Artificial Insemination and Genomics to Improve Global Swine Populations," Theriogenology, 2005, pp. 283-299, vol. 63.

Goryanin, I., et al., "Applications of Whole Cell and Large Pathway Mathematical Models in the Pharmaceutical Industry," Metabolic Engineering in the Post Genomic Era, 2004, p. 344.

Graham, C. F., "The Fusion of Cells with One- and Two-Cell Mouse Embryos," The Wistar Institute Symposium Monograph, 1969, pp. 19-33, vol. 9.

Hao, Y. H., et al., "Production of Endothelial Nitric Oxide Synthase (eNOS) Over-Expressing Piglets," Transgenic Research, 2006, pp. 739-750, vol. 15, No. 6.

Hauschild, J., et al., "Efficient Generation of a Biallelic Knockout in Pigs Using Zinc-Finger Nucleases," Proceedings of the National Academy of Sciences of the United States of America, 2011, pp. 12013-12017, vol. 108, No. 29.

Huang, Y. W., et a., "Porcine DC-SIGN: Molecular Cloning, Gene Structure, Tissue Distribution and Binding Characteristics," Developmental and Comparative Immunology, 2009, pp. 464-480, vol. 33.

Im, G.-S., et al., "In Vitro Development of Preimplantation Porcine Nuclear Transfer Embryos Cultured in Different Media and Gas Atmospheres," Theriogenology, 2004, pp. 1125-1135, vol. 61.

Keffaber, K. K., "Reproductive Failure of Unknown Etiology," American Association of Swine Practitioners Newsletter, 1989, pp. 1-9, vol. 1.

Kim, J.-K. et al., "Defining the Cellular Target(s) of Porcine Reproductive and Respiratory Syndrome Virus Blocking Monoclonal Antibody 7G10," Journal of Virology, Jan. 2006, pp. 689-696, vol. 80, No. 2.

Kolston, P. J., "Comparing in Vitro, In Situ, and In Vivo Experimental Data in A Three-Dimensional Model of Mammalian Cochlear Mechanics," Proceedings of the National Academy of Sciences of the United States of America, Mar. 1999, pp. 3676-3681, vol. 96, No. 7.

Kristiansen, M., et al., "Identification of the Haemoglobin Scavenger Receptor," Nature, 2001, pp. 198-201, vol. 409, No. 6817.

Lager, K. M., et al., "Evaluation of Protective Immunity in Gilts Inoculated with the NADC-8 Isolate of Porcine Reproductive and Respiratory Syndrome Virus (PRRSV) and Challenge-Exposed with an Antigenically Distinct PRRSV Isolate," American Journal of Veterinary Research, 1999, pp. 1022-1027, vol. 60, No. 8.

Lai, L., et al., "Generation of Cloned Transgenic Pigs Rich in Omega-3 Fatty Acids," Nature Biotechnology, 2006, pp. 435-436, vol. 24.

Lai, L. X., et al., "Production of Alpha-1,3-Galactosyltransferase Knockout Pigs by Nuclear Transfer Cloning," Science, 2002, pp. 1089-1092, vol. 295, No. 5557.

Lai, L., et al., "Alpha-1,3-Galactosyltransferase Knockout Pigs by Nuclear Transfer Cloning," Science, Feb. 2002, pp. 1089-1092, vol. 295, No. 5557.

Lai, L., et al., "Creating Genetically Modified Pigs by Using Nuclear Transfer," Reproductive Biology and Endocrinology, 2003, pp. 1-6, vol. 1, No. 82.

Lai, L., et al., "Generation of Cloned Transgenic Pigs Rich in Omega-3 Fatty Acids," Nature Biotechnology, Apr. 2006, pp. 435-436, vol. 24, No. 4.

Lai, L. et al., "Methods Paper—Production of Cloned Pigs by Using Somatic Cells as Donors," Cloning and Stem Cells, 2003, pp. 233-241, vol. 5, No. 4.

Lai, L. et al., "A Method for Producing Cloned Pigs by Using Somatic Cells as Donors," Methods in Molecular Biology, 2004, pp. 149-163, vol. 254.

Li, R., et al., "Cloned Transgenic Swine Via in Vitro Production and Cryopreservation," Biology of Reproduction, 2006, pp. 226-230, vol. 75, No. 2.

Lunney, J. K, et al., "Genetic Control of Host Resistance to Porcine Reproductive and Respiratory Syndrome Virus (PRRSV) Infection," Virus Research, 2010, pp. 161-169, vol. 154.

Machaty, Z., et al., "Complete Activation of Porcine Oocytes Induced by the Sulfhydryl Reagent, Thimerosal," Biology of Reproduction, 1997, pp. 1123-1127, vol. 57, No. 5.

Machaty, Z., et al., "Development of Early Porcine Embryos in Vitro and in Vivo," Biology of Reproduction, 1998, pp. 451-455, vol. 59.

Mansour, S. L., et al., "Disruption of the Proto-Oncogene int-2 in Mouse Embryo-Derived Stem Cells: A General Strategy for Targeting Mutations to Nonselectable Genes," Nature, 1988, pp. 348-352, vol. 336.

Mayes, M. A., et al., "Parthenogenic Activation of Pig Oocytes by Protein Kinase Inhibition," Biology of Reproduction, 1995, pp. 270-275, vol. 53, No. 2.

McGrath, J., et al., "Nuclear Transplantation in the Mouse Embryo by Microsurgery and Cell Fusion," Science, Jun. 1983, pp. 1300-1302, vol. 220, No. 4603.

Misinzo, G. M., et al., "Involvement of Proteases in Porcine Reproductive and Respiratory Syndrome Virus Uncoating Upon Internalization in Primary Macrophages," Veterinary Research, 2008, 14 pages, vol. 39, No. 55.

Whyte, J. J., et al., "Gene Targeting With Zinc Finger Nucleases to Produce Cloned eGFP Knockout Pigs," Molecular Reproduction and Development, Jan. 2011, p. 2, vol. 78, Issue 1.

(56) References Cited

OTHER PUBLICATIONS

Wikipedia, "In vitro," accessed from <https://en.wikipedia.orgiwiki/In_vitro> on Sep. 29, 2016, 6 pages.
Wills, R. W., et al., "Porcine Reproductive and Respiratory Syndrome Virus—A Persistent Infection," Veterinary Microbiology, 1997, pp. 231-240, vol. 55, Nos. 1-4.
Wissink, E. H. J., et al., "Identification of Porcine Alveolar Macrophage Glycoproteins Involved in Infection of Porcine Respiratory and Reproductive Syndrome Virus," Archives of Virology, 2003, pp. 177-187, vol. 148, No. 1.
Yang, D., et al., "Generation of PPAR(Gamma) Mono-Allelic Knockout Pigs Via Zinc-Finger Nucleases and Nuclear Transfer Cloning," Cell Research, 2011, pp. 979-982, vol. 6.
Yoon, I. L, et al., "Persistent and Contact Infection in Nursery Pigs Experimentally Infected with PRRS Virus," Swine Health and Production, 1993, pp. 5-8, vol. 1.
U.S. Appl. No. 15/216,865, filed Jul. 22, 2016.
U.S. Appl. No. 15/750,633, filed Feb. 6, 2018.
U.S. Appl. No. 62/658,740, filed Apr. 17, 2018.
Meng, X. J., "Heterogeneity of Porcine Reproductive and Respiratory Syndrome Virus: Implications for Current Vaccine Efficacy and Future Vaccine Development [Review]," Veterinary Microbiology, 2000, pp. 309-329, vol. 74, No. 4.
Meng, X. J., et al., "Sequence Comparison of Open Reading Frames 2 to 5 of Low and High Virulence United States Isolates of Porcine Reproductive and Respiratory Syndrome Virus," Journal of General Virology, 1995, pp. 3181-3188, vol. 76, Part 12.
Mengeling, W. L., et al., "Identification and Clinical Assessment of Suspected Vaccine-Related Field Strains of Porcine Reproductive and Respiratory Syndrome Virus," American Journal of Veterinary Research, 1999, pp. 334-340, vol. 60, No. 3.
Molitor, T. W., et al., "Immunity to PRRSV—Double-Edged Sword," Veterinary Microbiology, 1997, pp. 265-276, vol. 55, Nos. 1-4.
Murtaugh, M. P., et al., "Comparison of the Structural Protein Coding Sequences of the VR-2332 and Lelystad Virus Strains of the PRRS Virus," Archives of Virology, 1995, pp. 1451-1460, vol. 140, No. 8.
Nath, D., et al., "The Amino-Terminal Immunoglobulin-Like Domain of Sialoadhesin Contains the Sialic Acid Binding Bite, Comparison with CD22," The Journal of Biological Chemistry, 1995, pp. 26184-26191, vol. 270, No. 44.
Nauwynck, H. J., et al., "Entry of Porcine Reproductive and Respiratory Syndrome Virus into Porcine Alveolar Macrophages Via Receptor-Mediated Endocytosis," Journal of General Virology, 1999, pp. 297-305, vol. 80, Part 2.
Nelsen, C. J., et al., "Porcine Reproductive and Respiratory Syndrome Virus Comparison: Divergent Evolution on Two Continents," Journal of Virology, Jan. 1999, pp. 270-280, vol. 73, No. 1.
Nielsen, H. S., et al., "Generation of an Infectious Clone of VR-2332, A Highly Virulent North American-Type Isolate of Porcine Reproductive and Respiratory Syndrome Virus," Journal of Virology, Mar. 2003, pp. 3702-3711, vol. 77, No. 6.
Nielsen, M. J., et al., "The Macrophage Scavenger Receptor CD163: Endocytic Properties of Cytoplasmic Tail Variants," Journal of Leukocyte Biology, Apr. 2006, pp. 837-845, vol. 79, No. 4.
Nussbaum, D. J., et al., "Differential Effects of Protein Synthesis Inhibitors on Porcine Oocyte Activation," Molecular Reproduction and Development, 1995, pp. 70-75, vol. 41.
Oetke, C., et al., "Sialoadhesin-Deficient Mice Exhibit Subtle Changes in B- and T-Cell Populations and Reduced Immunoglobulin M Levels," Molecular and Cellular Biology, Feb. 2006, pp. 1549-1557, vol. 26, No. 4.
Park, K.-W., et al., "Developmental Potential of Porcine Nuclear Transfer Embryos Derived from Transgenic Fetal Fibroblasts Infected with the Gene for the Green Fluorescent Protein: Comparison of Different Fusion/Activation Conditions," Biology of Reproduction, 2001, pp. 1681-1685, vol. 65, No. 6.
Park, K.-W., et al., "Production of Nuclear Transfer-Derived Swine That Express the Enhanced Green Fluorescent Protein," Animal Biotechnology, 2001, pp. 173-181, vol. 12, No. 2.
Plagemann, P. G. W., "Lactate Dehydrogenase-Elevating Virus and Related Viruses," In Fields Virology, 3rd Edition, Fields, B et al., ed, 1996, Chapter 36, pp. 1105-1120.
Popescu, L., et al., "Genetically Edited Pigs Lacking CD163 Show No Resistance Following Infection with the African Swine Fever Virus Isolate, Georgia 200711," Virology, 2017, pp. 102-106, vol. 501.
Prather, R. S., et al., "An Intact Sialoadhesin (Sn/SIGLEC1/CD169) Is Not Required for Attachment/Internalization of the Porcine Reproductive and Respiratory Syndrome Virus," Journal of Virology, Sep. 2013, pp. 3538-9546, vol. 87, No. 17.
Rezaee, R., et al., "The Importance of Translatability in Drug Discovery," Expert Opinion on Drug Discovery, 2017, pp. 237-239, vol. 12, No. 3.
Ritter, M., et al., "The Scavenger Receptor CD163: Regulation, Promoter Structure and Genomic Organization," Pathobiology, 1999, pp. 257-261, vol. 67, Nos. 5-6.
Ritter, M., et al., "Genomic Organization and Chromosomal Localization of the Human CD163 (M130) Gene: A Member of the Scavenger Receptor Cysteine-Rich Superfamily," Biochemical and Biophysical Research Communications, 1999, pp. 466-474, vol. 260, No. 2.
Robl, J. M., et al., "Nuclear Transplantation in Bovine Embryos," Journal of Animal Science, Feb. 1987, pp. 342-647, vol. 64, No. 2.
Ropp, S. L., et al., "Characterization of Emerging European-Like Porcine Reproductive and Respiratory Syndrome Virus Isolates in the United States," Journal of Virology, Apr. 2004, pp. 3684-3703, vol. 78, No. 7.
Rowland, R. R. R., et al., "The Evolution of Porcine Reproductive and Respiratory Syndrome Virus: Quasispecies and Emergence of a Virus Subpopulation During Infection of Pigs with VR-2332," Virology, 1999, pp. 262-266, vol. 259.
Saeidnia, S., et al., "From in Vitro Experiments to in Vivo and Clinical Studies; Pros and Cons," Current Drug Discovery Technologies, 2015, pp. 218-224, vol. 12, No. 4.
Sanchez-Torres, C., et al., "Expression of Porcine CD163 on Monocytes/Macrophages Correlates with Permissiveness to African Swine Fever Infection," Archives of Virology, 2003, pp. 2307-2323, vol. 148, No. 12.
Sangamo BioSciences, Inc., "Sangamo BioSciences Announces Efficient Generation of Transgenic Pigs Using Zinc Finger Nuclease (ZFN) Technology," Press Release, Jul. 21, 2011, 2 pages.
Schurgers, E., et al., "Discrepancy Between the In Vitro and In Vivo Effects of Murine Mesenchymal Stem Cells on T-cell Proliferation and Collagen-Induced Arthritis," Arthritis Research & Therapy, 2010, pp. 1-11, vol. 12, No. 1.
Shanmukhappa, K., et al., "Role of CD151, A Tetraspanin, In Porcine Reproductive and Respiratory Syndrome Virus Infection," Virology Journal, 2007, pp. 1-12, vol. 4, No. 62.
Snijder, E. J., et al., "The Molecular Biology of Arteriviruses [Review]," Journal of General Virology, 1998, pp. 961-979, vol. 79, Part 5.
Stephen, S. L., et al., "Scavenger Receptors and Their Potential as Therapeutic Targets in the Treatment of Cardiovascular Disease," International Journal of Hypertension, 2010, 21 pages, vol. 2010, Article ID 646929.
Suarez, P., et al., "Open Reading Frame 5 of Porcine Reproductive and Respiratory Syndrome Virus as a Cause of Virus-Induced Apoptosis," Journal of Virology, May 1996, pp. 2876-2882, vol. 70, No. 5.
Sur, J. H., et al., "In Vivo Detection of Porcine Reproductive and Respiratory Syndrome Virus RNA by in Situ Hybridization at Different Times Postinfection," Journal of Clinical Microbiology, Sep. 1996, pp. 2280-2286, vol. 34, No. 9.
Sur, J. H., et al., "Porcine Reproductive and Respiratory Syndrome Virus Replicates in Testicular Germ Cells, Alters Spermatogenesis, and Induces Germ Cell Death by Apoptosis," Journal of Virology, Dec. 1997, pp. 9170-9179, vol. 71, No. 12.
Vadori, M., et al., "The Immunological Barriers to Xenotransplantation," Tissue Antigens, 2015, pp. 239-253, vol. 86, No. 4.
Van Breedam, W., et al., "Porcine Reproductive and Respiratory Syndrome Virus Entry into the Porcine Macrophage," Journal of General Virology, 2010, pp. 1659-1667, vol. 91, Part 7.

(56) References Cited

OTHER PUBLICATIONS

Van Breedam, W., et al., "The M/GP(5) Glycoprotein Complex of Porcine Reproductive and Respiratory Syndrome Virus Binds the Sialoadhesin Receptor in a Sialic Acid-Dependent Manner," PLoS Pathogens, 2010, e1000730, pp. 1-11, vol. 6, No. 1.

Van Den Hoff, M. J. B., et al., "Electroporation in 'Intracellular' Buffer Increases Cell Survival," Nucleic Acids Research, 1992, p. 2902, vol. 20, No. 11.

Van Gorp, H., et al., "Identification of the CD163 Protein Domains Involved in Infection of the Porcine Reproductive and Respiratory Syndrome Virus," Journal of Virology, Supplemental Material, Mar. 2010, 4 pages, vol. 84, No. 6, Accessed from <http://jvi.asm.org/content/84/6/3101/suppl/DC1>.

Van Gorp, H., et al., "Identification of the CD163 Protein Domains Involved in Infection of the Porcine Reproductive and Respiratory Syndrome Virus," Journal of Virology, Mar. 2010, pp. 3101-3105, vol. 84, No. 6.

Van Gorp, H., et al., "Sialoadhesin and CD163 Join Forces During Entry of the Porcine Reproductive and Respiratory Syndrome Virus," Journal of General Virology, 2008, pp. 2943-2953, vol. 89, Part 12.

Van Gorp, H., et al., "Scavenger Receptor CD163, A Jack-of-all-trades and Potential Target for Cell-Directed Therapy," Molecular Immunology, 2010, pp. 1650-1660, vol. 47, Nos. 7-8.

Vanderheijden, N., et al., "Involvement of Sialoadhesin in Entry of Porcine Reproductive and Respiratory Syndrome Virus into Porcine Alveolar Macrophages," Journal of Virology, Aug. 2003, pp. 8207-8215, vol. 77, No. 15.

Vinson, M., et al., "Characterization of the Sialic Acid-Binding Site in Sialoadhesin by Site-Directed Mutagenesis," Journal of Biological Chemistry, 1996, pp. 9267-9272, vol. 271, No. 16.

Watanabe, M., et a.., "Knockout of Exogenous EGFP Gene in Porcine Somatic Cells Using Zinc-finger Nucleases," Biochemical and Biophysical Research Communications, Nov. 2010, pp. 14-18, vol. 402, Issue 1.

Welch, S. K. W., et al., "A Brief Review of CD163 and its Role in PRRSV Infection," Virus Research, 2010, pp. 98-103, vol. 154.

Wensvoort, G., et al., "Mystery Swine Disease in the Netherlands: The Isolation of Lelystad Virus," Veterinary Quarterly, 1991, pp. 121-130, vol. 13.

Whitworth, K M., et al., "Gene-edited Pigs are Protected From Porcine Reproductive and Respiratory Syndrome Virus," Nature Biotechnology, Jan. 2016, pp. 20-22, vol. 34, No. 1.

Whitworth, K M., et al., "Disruption the Sialoadhesin and CD163 Genes to Create Pigs Resistant to PRRSV Infectivity," Abstract, Swine in Biomedical Research in Chicago, Illinois, Jul. 17-19, 2011, S1-25, pp. 39-40.

Whitworth, K M., et al., "Pigs Resistant to PRRSV Infectivity," Poster Presented at Swine in Biomedical Research in Chicago, Illinois, Jul. 18, 2011, 1 page.

Aigner, B., et al., "Transgenic Pigs as Models for Translational Biomedical Research," Journal of Molecular Medicine, 2010, pp. 653-664, vol. 88, No. 7.

Bookstein, R., et al., "Promoter Deletion and Loss of Retinoblastoma Gene Expression in Human Prostate Carcinoma," Proceedings of the National Academy of Sciences of the United States of America, Oct. 1990, pp. 7762-7766, vol. 87, No. 19.

Chin, K-K., et al., "The sup(-104)G Nucleotide of the Human CYP21 Gene is Important for CYP21 Transcription Activity and Protein Interaction," Nucleic Acids Research, 1998, pp. 1959-1964, vol. 26, No. 8.

Ciotti, M., et al., "Coding Defect and A TATA Box Mutation at the Bilirubin UDP-Glucuronosyltransferase Gene Cause Crigler-Najjar Type I Disease," Biochimica et Biophysica ACTA, 1998, pp. 40-50, vol. 1407.

Flagiello, L., et al., "Mutation in the Nerve-Specific 5'non-coding Region of Cx32 Gene and Absence of Specific mRNA in A CMTX1 Italian Family," Human Mutation, 1998, p. 361, vol. 12, No. 5, Abstract Only.

Hyder, S. M., et al., "Identification of an Estrogen Response Element in the 3'-Flanking Region of the Murine c-fos Protooncogene," The Journal of Biological Chemistry, 1992, pp. 18047-18054, vol. 267, No. 25.

Kleinjan, D.-J., et al., "Cis-ruption Mechanisms: Disruption of cis-regulatory Control as A Cause of Human Genetic Disease," Briefings in Functional Genomics and Proteomics, 2009, pp. 317-332, vol. 8, No. 4.

Li, Y., et al., "Regulation of Human NAD(P)H:Quinone Oxidoreductase Gene," The Journal of Biological Chemistry, 1992, pp. 15097-15104, vol. 267, No. 21.

Loudianos, G., et al., "Molecular Characterization of Wilson Disease in the Sardinian Population—Evidence of A Founder Effect," Human Mutation, 1999, pp. 294-303, vol. 14, No. 4, Abstract Only.

Menon, K. P., et al., "Architecture of the Canine IDUA Gene and Mutation Underlying Canine Mucopolysaccharidosis 1.," Genomics, 1992, pp. 763-768, vol. 14, No. 3, Abstract Only.

* cited by examiner

Organization of the sialoadhesin gene and targeting vector design.

Organization of the sialoadhesin gene and targeting vector design.

PCR screening to identify targeting of the sialoadhesin gene.

PCR screening to identify the equal presence of both wildtype and targeted sialoadhesin alleles.

PORCINE REPRODUCTIVE AND RESPIRATORY SYNDROME VIRUS RESISTANT ANIMALS

REFERENCE TO RELATED APPLICATIONS

This application is a continuation of U.S. patent application Ser. No. 15/783,417, filed Oct. 13, 2017, which is a continuation of U.S. patent application Ser. No. 14/117,943, filed Nov. 15, 2013, now issued as U.S. Pat. No. 9,820,475, which is a U.S. national stage application of International Patent Application No. PCT/US2012/038193, filed May 16, 2012, which claims the benefit of U.S. Provisional Application Ser. No. 61/519,076, filed May 16, 2011. Each of the above-cited applications is incorporated by reference herein in its entirety.

GOVERNMENT SUPPORT

This invention was made with Government support under the contract number (USDA/ARS) 58-1940-8-868 awarded by THE Department of Agriculture. The Government has certain rights in the invention.

SEQUENCE LISTING

This application contains a Sequence Listing entitled "UMO 11053.WO SEQ_ST25" generated on May 15, 2012, which is hereby incorporated by reference in its entirety.

FIELD OF THE INVENTION

The present invention generally relates to genetically modified swine wherein at least one allele of a SIGLEC1 gene has been inactivated and/or at least one allele of a CD163 gene has been inactivated. Methods for producing such transgenic swine are also provided.

BACKGROUND OF THE INVENTION

Porcine Reproductive and Respiratory Syndrome (PRRS) is one of the most economically important diseases of swine. This disease was first detected in the United States in 1987 (Keffaber 1989) and in Europe in 1990 (Wensvoort et al. 1991). Molecular analysis of the prototype PRRS viruses (PRRSV) VR-2332 and Lelystad (U.S. and European isolates, respectively) has suggested that divergently evolved strains emerged on two continents almost simultaneously, perhaps due to similar changes in swine management practices (Murtaugh et al. 1995; Nelsen et al. 1999). Since its initial emergence, this virus has spread worldwide, and PRRSV of the European genotype has been detected in U.S. swine herds (Ropp et al. 2004). PRRS is characterized by severe and sometimes fatal respiratory disease and reproductive failure, but also predisposes infected pigs to bacterial pathogens as well as other viral pathogens (Benfield et al. 1992), and is a key component of the economically significant Porcine Respiratory Disease Complex (PRDC). The most consistent pathological lesions caused by PRRSV during acute infection are interstitial pneumonia and mild lymphocytic encephalitis (Plagemann 1996). After the acute phase of PRRSV infection, which is typically characterized by viremia and clinical disease, many pigs fully recover yet carry a low-level viral infection for an extended period of time. These "carrier" pigs are persistently infected with PRRSV and shed the virus, either intermittently or continuously, and may infect naïve pigs following direct or indirect contact. Under experimental conditions, persistent infection with PRRSV has been well documented (Albina et al. 1994; Allende et al. 2000; Benfield et al. 1998; Christopherhennings et al. 1995; Sur et al. 1996; Yoon et al. 1993). Most notably, infectious virus has been recovered for up to 157 days post-infection (Wills et al. 1997). Tissue macrophages and monocytes are the major target cells during both acute and persistent infection (Molitor et al. 1997), although pneumocytes and epithelial germ cells of the testes have also been shown to be infected (Sur et al. 1996; Sur et al. 1997).

The etiologic agent of PRRS is an enveloped, positive-stranded RNA virus that is a member of the Arteriviridae family, order Nidovirales. Other members of the Arteriviridae include Lactate dehydrogenase-elevating virus (LDV) of mice, Equine arteritis virus (EAV), and Simian hemorrhagic fever virus (SHFV). Analysis of genomic sequence data reveals extensive diversity among strains of PRRSV but also well-conserved domains (Andreyev et al. 1997; Meng 2000; Meng et al. 1995). The genome organization of PRRSV is similar to that of other Arteriviruses, with the genomic RNA functioning as the messenger RNA for the ORF1a replicase proteins (Plagemann 1996). ORFs1a and 1b comprise approximately 80% of the viral genome and encode the RNA-dependent RNA polymerase as well as polyproteins that are processed into other nonstructural proteins (Snijder and Meulenberg 1998). Using Lelystad virus, ORFs 2-7 have been determined to encode the viral structural proteins. The protein encoded by ORF 5 (GP5) and M (Van Breedam et al. 2010b) may play a role in the induction of apoptosis by PRRSV (Suarez et al. 1996; Sur et al. 1997) and is thought to be the viral attachment protein in the closely related Lactate dehydrogenase-elevating virus. The minor envelope glycoproteins GP2a and GP4 of the PRRSV interact with CD163 (Das et al. 2010). There are data suggesting that binding to SIGLEC1 (sialic acid binding Ig-like lectin 1) is necessary for entry into the cells, and in fact dual binding to both SIGLEC1 and CD163 appears to be needed for viral infection (Van Gorp et al. 2008).

Many characteristics of both PRRSV pathogenesis (especially at the molecular level) and epizootiology are poorly understood thus making control efforts difficult. To gain a better understanding, infectious clones for PRRSV have been developed (Nielsen et al. 2003). Today producers often vaccinate swine against PRRSV with modified-live attenuated strains or killed virus vaccines. However, current vaccines often do not provide satisfactory protection, due to both the strain variation and inadequate stimulation of the immune system. A protective immune response is possible since it has been demonstrated that previous exposure can provide complete protection when pigs are challenged with a homologous strain of PRRSV (Lager et al. 1999). However, protective immunity has never been consistently demonstrated for challenge with heterologous strains. In addition to concerns about the efficacy of the available PRRSV vaccines, there is strong evidence that the modified-live vaccine currently in use can persist in individual pigs and swine herds and accumulate mutations (Mengeling et al. 1999), as has been demonstrated with virulent field isolates following experimental infection of pigs (Rowland et al. 1999). Furthermore, it has been shown that vaccine virus is shed in the semen of vaccinated boars (Christopherhennings et al. 1997). As an alternative to vaccination, some experts are advocating a "test and removal" strategy in breeding herds (Dee and Molitor 1998). Successful use of this strategy depends on removal of all pigs that are either acutely or persistently infected with PRRSV, followed by strict controls to prevent reintroduction of the virus. The difficulty, and much of the expense, associated with this strategy is that there is little known about the pathogenesis of persistent PRRSV infection and thus there are no reliable techniques to identify persistently infected pigs.

A putative cellular receptor for PRRSV has been identified by monoclonal antibodies, purified and sequenced (Vanderheij den et al. 2003; Wissink et al. 2003) and named SIGLEC1. This molecule has similarity to sialoadhesins and was shown to mediate entry of PRRSV into non-susceptible cells but a recombinant cell line expressing this receptor failed to support productive replication of PRRSV (Vanderheijden et al. 2003). Importantly, the sialic acid molecules present on the PRRSV surface have been shown to be needed for infection of alveolar macrophages. Following viral binding to this receptor, entry of PRRSV occurs by receptor-mediated endocytosis (Nauwynck et al. 1999). The key role of sialoadhesin for PRRSV entry was established by experiments in which viral uptake was demonstrated in PK15 cells (a cell line non-permissive for PRRSV replication) that were transfected with cloned porcine sialoadhesin, but not in un-transfected control PK15 cells (Vanderheij den et al. 2003). Further research by this same group demonstrated that interactions between the sialic acid on the PRRSV virion surface and the sialoadhesin molecule were essential for PRRSV infection of alveolar macrophages (Delputte and Nauwynck 2004). A reverse strategy, i.e. removing the sialic acid on the surface of the PRRSV or preincubation with sialic acid-specific lectins also resulted in blocking of the infection (Delputte et al. 2004; Delputte and Nauwynck 2004; Van Breedam et al. 2010b). Independent of the specific research on PRRSV entry, site-directed mutagenesis has been used to identify six key amino acid residues required for sialic acid binding by murine sialoadhesin (Vinson et al. 1996), which is 69% identical to porcine sialoadhesin. Importantly, all six amino acids identified in murine sialoadhesin are also conserved in the porcine molecule.

SIGLEC1 is a transmembrane receptor of a family of sialic acid binding immunoglobulin-like lectins. It was first described as a sheep erythrocyte binding receptor of mouse macrophages (Crocker and Gordon 1986). It is expressed on macrophages in hematopoietic and lymphoid tissues. SIGLECs consist of an N-terminal V-set domain containing the sialic acid binding site followed by a variable number of C2-set domains, and then a transmembrane domain and a cytoplasmic tail. In contrast to other SIGLECs, SIGLEC1 does not have a tyrosine-based motif in the cytoplasmic tail (Oetke et al. 2006). The sialic acid-binding site was mapped to the N-terminal immunoglobulin-like V-set domain (Nath et al. 1995). The R116 residue appears to be one of the important amino acids for sialic acid binding (Crocker et al. 1999; Delputte et al. 2007). Thus, an intact N-terminal domain is both necessary and sufficient for PRRSV binding to SIGLEC1 (Van Breedam et al. 2010a). A knockout of SIGLEC1 was reported in mice and resulted in mice that were viable and fertile and showed no developmental abnormalities (Oetke et al. 2006). However, these mice had subtle changes in B- and T-cell populations and a reduced immunoglobulin M level.

The infection process of the PRRSV begins with initial binding to heparan sulfate on the surface of the alveolar macrophage. Secure binding then occurs to sialoadhesin (SIGLEC1, also referred to as CD169 or SN). The virus is then internalized via clatherin-mediated endocytosis. Another molecule, CD163, then facilitates the uncoating of the virus in the endosome (Van Breedam et al. 2010a). The viral genome is released and the cell infected.

CD163 has 17 exons and the protein is composed of an extracellular region with 9 scavenger receptor cysteine-rich (SRCR) domains, a transmembrane segment, and a short cytoplasmic tail. Several different variants result from differential splicing of a single gene (Ritter et al. 1999a; Ritter et al. 1999b). Much of this variation is accounted for by the length of the cytoplasmic tail.

CD163 has a number of important functions, including acting as a haptoglobin-hemoglobin scavenger receptor. Elimination of free hemoglobin in the blood is an important function of CD163 as the heme group can be very toxic (Kristiansen et al. 2001). CD163 has a cytoplasmic tail that facilitates endocytosis. Mutation of this tail results in decreased haptoglobin-hemoglobin complex uptake (Nielsen et al. 2006). Other functions of C163 include erythroblast adhesion (SRCR2), being a TWEAK receptor (SRCR1-4 & 6-9), a bacterial receptor (SRCRS), an African Swine Virus receptor (Sanchez-Torres et al. 2003), and a potential role as an immune-modulator (discussed in (Van Gorp et al. 2010a)).

SUMMARY OF THE INVENTION

In one aspect, the present invention is a genetically modified swine wherein at least one allele of a SIGLEC1 gene has been inactivated and/or at least one allele of a CD163 gene has been inactivated, wherein inactivation of the CD163 allele results in a CD163 protein which cannot bind and/or uncoat a porcine reproductive and respiratory syndrome virus (PRRSV).

Another aspect of the present invention is a genetically modified swine wherein at least one allele of a SIGLEC1 gene has been inactivated, produced by a method comprising enucleating a swine oocyte; fusing the oocyte with a donor swine fibroblast cell, the genome of the fibroblast cell comprising at least one inactivated SIGLEC1 allele; and activating the oocyte to produce an embryo.

The present invention also relates to a genetically modified swine wherein at least one allele of a CD163 gene has been inactivated, wherein inactivation of the CD163 allele results in a CD163 protein which cannot bind and/or uncoat a porcine reproductive and respiratory syndrome virus (PRRSV), produced by a method comprising enucleating a swine oocyte; fusing the oocyte with a donor swine fibroblast cell, the genome of the fibroblast cell comprising at least one inactivated CD163 allele; and activating the oocyte to produce an embryo.

In another aspect, the present invention is a genetically modified swine wherein both alleles of a SIGLEC1 gene have been inactivated, produced by a method comprising mating a male genetically modified swine wherein at least one allele of the SIGLEC1 gene has been inactivated with a female genetically modified swine wherein at least one allele of the SIGLEC1 gene has been inactivated to produce F1 progeny, and screening the F1 progeny to identify genetically modified swine wherein both alleles of the SIGLEC1 gene have been inactivated.

It is another aspect of the present invention to provide a genetically modified swine wherein both alleles of a CD163 gene have been inactivated, produced by a method comprising mating a male genetically modified swine wherein at least one allele of the CD163 gene has been inactivated with a female genetically modified swine wherein at least one allele of the CD163 gene has been inactivated to produce F1 progeny, and screening the F1 progeny to identify genetically modified swine wherein both alleles of the CD163 gene have been inactivated.

The present invention also relates to a genetically modified swine wherein both alleles of a SIGLEC1 gene and both alleles of a CD163 gene have been inactivated, wherein inactivation of the CD163 allele results in a CD163 protein which cannot bind and/or uncoat a porcine reproductive and respiratory syndrome virus (PRRSV), which is produced by any of three methods. The first such method comprises mating a genetically modified swine having at least one inactivated SIGLEC1 allele with a genetically modified swine having at least one inactivated CD163 allele to produce F1 progeny, and screening the F1 progeny to identify genetically modified swine wherein at least one allele of the SIGLEC1 gene has been inactivated and at least one allele of the CD163 gene has been inactivated. This method further comprises mating the genetically modified swine wherein at least one allele of the SIGLEC1 gene has been inactivated and at least one allele of the CD163 gene has been inactivated to each other to produce F2 progeny and screening the F2 progeny to identify genetically modified swine wherein both alleles of the SIGLEC1 gene and both alleles of the CD163 gene have been inactivated.

The second such method comprises mating a genetically modified swine wherein both alleles of a SIGLEC1 gene have been inactivated with a genetically modified swine wherein both alleles of a CD163 gene have been inactivated to produce F1 progeny, mating the F1 progeny to produce F2 progeny, and screening the F2 progeny to identify genetically modified swine wherein both alleles of the SIGLEC1 gene and both alleles of the CD163 gene have been inactivated.

The third such method comprises mating a genetically modified swine wherein at least one allele of a SIGLEC1 gene and at least one allele of a CD163 gene have been inactivated to another genetically modified swine wherein at least one allele of a SIGLEC1 gene and at least one allele of a CD163 gene have been inactivated to produce F1 progeny, and screening the F1 progeny to identify genetically modified swine wherein both alleles of the SIGLEC1 gene and both alleles of the CD163 gene have been inactivated.

The present invention also relates to progeny any of the above-described genetically modified swine, wherein: (1) at least one allele of a SIGLEC1 gene has been inactivated; (2) at least wherein at least one allele of a CD163 gene has been inactivated; (3) at least one allele of a SIGLEC1 gene and at least one allele of a CD163 gene have been inactivated; or (4) both alleles of a SIGLEC1 gene and both alleles of a CD163 gene have been inactivated. In such progeny wherein one or both alleles of a CD163 gene have been inactivated, the inactivation of results in a CD163 protein which cannot bind and/or uncoat a porcine reproductive and respiratory syndrome virus (PRRSV).

The present invention is also directed to a method for producing a genetically modified swine wherein at least one allele of a SIGLEC1 gene has been inactivated. The method comprises enucleating a swine oocyte; fusing the oocyte with a donor swine fibroblast cell, the genome of the fibroblast cell comprising at least one inactivated SIGLEC1 allele; and activating the oocyte to produce an embryo.

In still another aspect, the present invention is a method for producing a genetically modified swine wherein at least one allele of a CD163 gene has been inactivated, wherein inactivation of the CD163 allele results in a CD163 protein which cannot bind and/or uncoat a porcine reproductive and respiratory syndrome virus (PRRSV). This method comprises enucleating a swine oocyte; fusing the oocyte with a donor swine fibroblast cell, the genome of the fibroblast cell comprising at least one inactivated CD163 allele; and activating the oocyte to produce an embryo.

The present invention is also directed to a method for producing a genetically modified swine wherein both alleles of a SIGLEC1 gene have been inactivated. The method comprises mating a female genetically modified swine having at least one inactivated SIGLEC1 allele with a male genetically modified swine having at least one inactivated SIGLEC1 allele to produce F1 progeny, and screening the F1 progeny to identify genetically modified swine wherein both alleles of the SIGLEC1 gene have been inactivated.

The present invention is also directed to a method for producing a genetically modified swine wherein both alleles of a CD163 gene have been inactivated, wherein inactivation of the CD163 allele results in a CD163 protein which cannot bind and/or uncoat PRRSV. This method comprises mating a female genetically modified swine having at least one inactivated CD163 allele with a male genetically modified swine having at least one inactivated CD163 allele to produce F1 progeny, and screening the F1 progeny to identify genetically modified swine wherein both alleles of the CD163 gene have been inactivated.

Another aspect of the present invention is a method for producing a genetically modified swine wherein both alleles of a SIGLEC1 gene and both alleles of a CD163 gene have been inactivated, wherein inactivation of the CD163 alleles results in a CD163 protein which cannot bind and/or uncoat a porcine reproductive and respiratory syndrome virus (PRRSV). The method comprises mating a genetically modified swine having at least one inactivated SIGLEC1 allele with a genetically modified swine having at least one inactivated CD163 allele to produce F1 progeny, and screening the F1 progeny to identify genetically modified swine wherein at least one allele of the SIGLEC1 gene has been inactivated and at least one allele of the CD163 gene has been inactivated. The method further comprises mating the genetically modified swine wherein at least one allele of the SIGLEC1 gene has been inactivated and at least one allele of the CD163 gene has been inactivated to each other to produce F2 progeny and screening the F2 progeny to identify genetically modified swine wherein both alleles of the SIGLEC1 gene and both alleles of the CD163 gene have been inactivated.

The present invention also relates to another method for producing a genetically modified swine wherein both alleles of a SIGLEC1 gene and both alleles of a CD163 gene have been inactivated, wherein inactivation of the CD163 gene results in a CD163 protein which cannot bind and/or uncoat a porcine reproductive and respiratory syndrome virus (PRRSV). This method comprises mating a genetically modified swine wherein both alleles of a SIGLEC1 gene have been inactivated with a genetically modified swine wherein both alleles of a CD163 gene have been inactivated to produce F1 progeny, mating the F1 progeny to produce F2 progeny, and screening the F2 progeny to identify genetically modified swine wherein both alleles of the SIGLEC1 gene and both alleles of the CD163 gene have been inactivated.

The present invention is also directed to yet another method for producing a genetically modified swine wherein both alleles of a SIGLEC1 gene and both alleles of a CD163 gene have been inactivated, wherein inactivation of the CD163 gene results in a CD163 protein which cannot bind and/or uncoat a porcine reproductive and respiratory syndrome virus (PRRSV). The method comprises mating a genetically modified swine wherein at least one allele of a SIGLEC1 gene and at least one allele of a CD163 gene have been inactivated to another genetically modified swine wherein at least one allele of a SIGLEC1 gene and at least one allele of a CD163 gene have been inactivated to produce F1 progeny, and screening the F1 progeny to identify genetically modified swine wherein both alleles of the SIGLEC1 gene and both alleles of the CD163 gene have been inactivated.

In other aspects, the present invention relates to progeny of genetically modified swine produced by any of the above methods, wherein one or both alleles of a SIGLEC1 gene have been inactivated and/or wherein one or both alleles of a CD163 gene have been inactivated, wherein inactivation of the CD163 alleles results in a CD163 protein which cannot bind and/or uncoat a porcine reproductive and respiratory syndrome virus (PRRSV).

Other objects and features will be in part apparent and in part pointed out hereinafter.

DEFINITIONS

Figure 1:
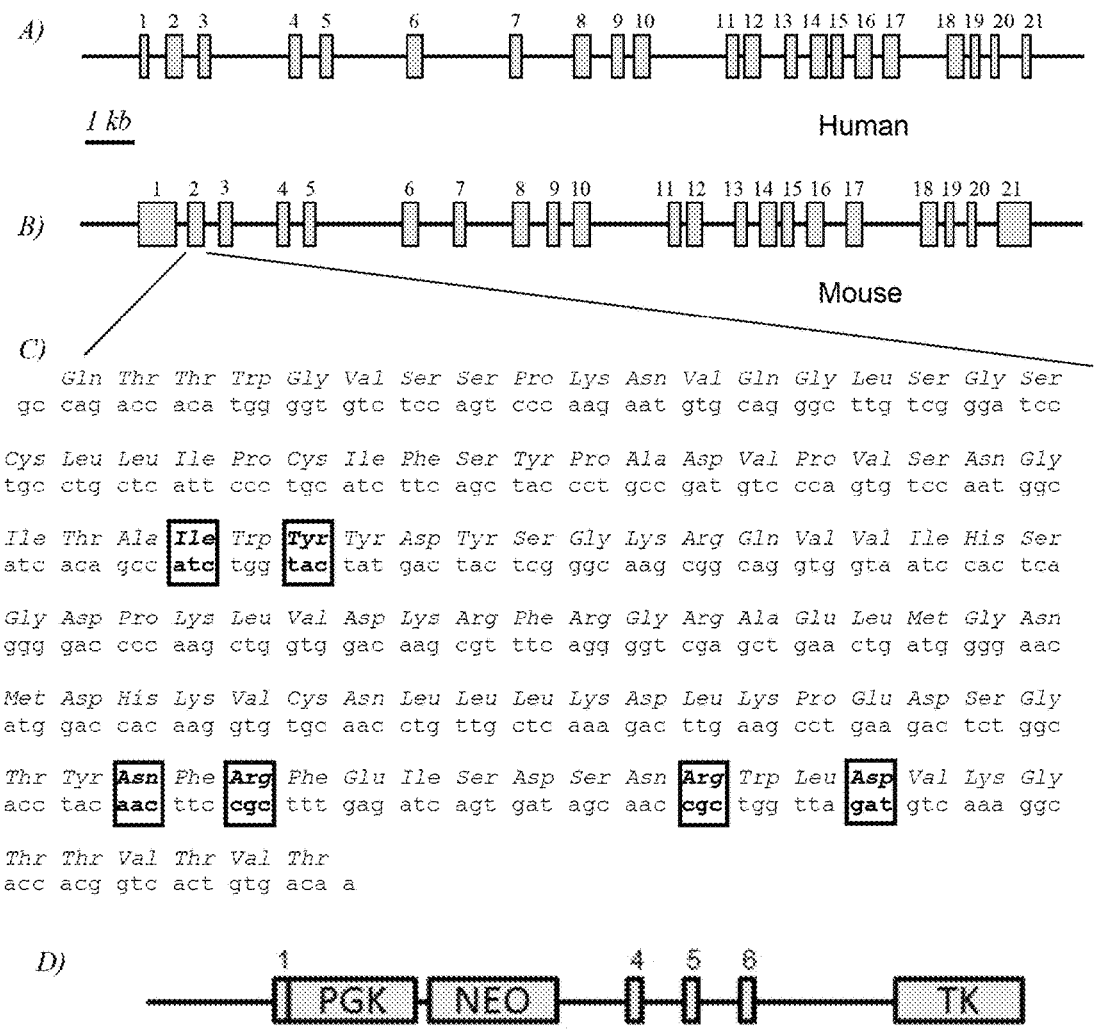
FIG. 1 depicts the organization of the sialoadhesin gene and the targeting vector design. Panels A and B of FIG. 1 are schematic diagrams showing that the human (panel A) and mouse (panel B) sialoadhesin genes respectively are composed of 21 exons and span approximately 20 kb. Panel C of FIG. 1 shows murine mutational analyses of exon 2 (the DNA sequence of exon 2 as shown in panel C of FIG. 1 is SEQ ID NO: 7, and the amino acid sequence encoded by exon 2 as shown in panel C of FIG. 1 is SEQ ID NO: 8). The mutational analysis revealed 6 amino acids that conferred binding of sialoadhesin to ligand (shown in boxed/bold text). Panel D of FIG. 1 depicts a targeting vector design that was used to replace part of exon 1 and exons 2 and 3 of SIGLEC1 with stop codons. The vector also included a neomycin (neo) selection cassette driven by a PGK promoter.

A "knockout swine" is a genetically modified swine in which the function of one or both alleles of a gene has been altered, for example, by partial or complete gene deletion. If one allele of a gene is knocked out, the swine is heterozygous for that gene knock-out; if both alleles are knocked out, the swine is homozygous for the gene knockout.

The term "donor cell" refers to a cell from which a nucleus or chromatin material is derived, for use in nuclear transfer. As is discussed elsewhere herein, nuclear transfer can involve transfer of a nucleus or chromatin only as isolated from a donor cell, or transfer of an entire donor cell including such a nucleus or chromatin material.

The term "genetic modification" refers to one or more alterations in a gene sequence (including coding sequences and non-coding sequences, such as introns, promoter sequences, and 5' and 3'-untranslated sequences) that alter the expression or activity of the gene. Such modifications include, for example, insertions (of, e.g., heterologous sequences, such as selectable markers, and/or termination signals), deletions, frame shift mutations, nonsense mutations, missense mutations, point mutations, or combinations thereof.

The term "recipient cell" refers to a cell into which a donor cell, a donor cell nucleus, or donor cell chromatin is introduced. Recipient cells are suitably enucleated prior to nuclear transfer. Examples of recipient cells include oocytes, zygotes, and the cells of two-cell embryos.

"Small interfering RNA" (siRNA) refers to double-stranded RNA molecules which have the ability to specifically interfere with protein expression. siRNAs are generally from about 10 to about 30 nucleotides in length. The length of the siRNA molecule is based on the length of the antisense strand of the siRNA molecule.

DESCRIPTION OF THE PREFERRED EMBODIMENTS

The present invention is directed to genetically modified swine which are resistant to infection by porcine respiratory and reproductive syndrome virus (PRRSV). PRRSV infectivity results from three specific entry mediators: (1) initial binding with heparan sulfate, (2) binding/internalization by sialoadhesin (SIGLEC1), and (3) internalization/uncoating of the virus by CD163. Thus, prevention of interaction between PRRSV and SIGLEC1 and/or PRRSV and CD163 results in the inability of PRRSV to establish the infection in a host. As such, the present invention is directed to genetically modified swine, wherein at least one allele of a SIGLEC1 gene has been inactivated and/or wherein at least one allele of a CD163 gene has been inactivated, wherein inactivation of the CD163 allele results in a CD163 protein which cannot bind and/or uncoat a porcine reproductive and respiratory syndrome virus (PRRSV). These swine can also be referred to as swine knockouts for SIGLEC1 and/or CD163.

The invention includes swine in which only one allele of a targeted gene (SIGLEC1 and/or CD163) has been inactivated, while the other allele has remained unaffected. These animals, which are referred to herein as "heterozygous" or "hemizygous" animals can be used in breeding approaches to generate homozygous mutants. Also included in the invention are homozygous mutant swine, in which both alleles of a target gene are inactivated, either by the same or by different approaches. Accordingly, the present invention includes genetically modified swine wherein: (1) one allele of a SIGLEC1 gene has been inactivated; (2) one allele of a CD163 gene has been inactivated; (3) both alleles of a SIGLEC1 gene have been inactivated; (4) both alleles of a CD163 gene have been inactivated; (5) both alleles of a SIGLEC1 gene and one allele of a CD163 gene have been inactivated; (6) one allele of a SIGLEC1 gene and both alleles of a CD163 gene have been inactivated; (7) one allele of a SIGLEC1 gene and one allele of a CD163 gene have been inactivated; or (8) both alleles of a SIGLEC1 gene and both alleles of a CD163 gene have been inactivated. In each of these instances and in the context of the present application generally, the inactivation of the CD163 allele(s) results in a CD163 protein which cannot bind and/or uncoat a porcine reproductive and respiratory syndrome virus (PRRSV).

Gene targeting carried out to make the animals of the invention can result in gene inactivation by disruption, removal, modification, or replacement of target gene sequences. Methods for gene inactivation are well known in the art. For example, a target gene can be inactivated by the insertion of a heterologous sequence (such as a selectable marker and/or a stop codon) into a target gene, deletion of a part of a gene or the entire gene, modification of a gene (e.g., by frame shift mutation, nonsense mutation, missense mutation, point mutation, replacement of a part or a whole gene with another nucleic acid sequence), or a combination of any of the above.

Inserted sequences can replace previously existing sequences in a gene or can be added to such sequences, depending on the design of the targeting construct. The design of targeting constructs can be altered, depending upon whether it is desired to completely knock out the function of a gene or to maintain some reduced level of function. In the case of SIGLEC1, complete knock out of function is desirable. By way of example and not of limitation, the SIGLEC1 gene can be knocked out by deletion of part of exon 1 and all of exons 2 and 3, for example by replacing part of exon 1 and all of exons 2 and 3 with a neomycin selectable cassette. In some embodiments, the modification can also include the addition of LoxP sites on either side of a sequence of a SIGLEC1 gene that is to be mutated. In some instances, the targeting construct can contain both the loxP sites flanking a sequence to be inserted and the CRE recombinase. In other cases, a two-vector system can be used, wherein the targeting construct includes the loxP sites flanking a sequence to be inserted and a second vector includes a transgene encoding for the CRE recombinase. The transgene for CRE recombinase can be placed under the influence of a tissue-specific promoter, such that its expression renders the SIGLEC1 gene non-functional in specific cell lineages. Similarly, the antibiotic selectable cassette can be flanked by loxP sites so that it can be deleted at a later stage using the Cre recombinase.

In the case of CD163, it is desirable to only inactivate its function related to PRRSV binding and/or uncoating while leaving the other functions of CD163 minimally affected or unaffected. While not being bound to any particular theory, it is believed that a complete CD163 knock-out may not be viable or could be seriously compromised due to the role of CD163 in binding and internalization of haemoglobin-haptoglobin complexes. Accordingly, CD163 can be inactivated by disrupting the fifth N-terminal scavenger receptor cysteine-rich (SRCR) domain of CD163, which was previously shown to play a leading role in PRRSV infection (Van Gorp et al., 2010), while leaving the other domains unaffected. SRCR domain 5 can be genetically modified by, e.g., introducing point mutations which alter the structure of this domain or by swapping this domain with another one. For example, SRCR domain 5 can be replaced with SRCR domain 8 from CD163 Ligand (CD163L) since this domain "swap" has been shown to reduce relative PRRSV infectivity to 0% in cultured cells (Van Gorp et al 2010).

In other approaches, the coding sequences for a target gene are not altered or are minimally altered and, rather, sequences impacting expression of a target gene, such as promoter sequences, are targeted. In any case, selectable marker insertion is often desirable to facilitate identification of cells in which targeting has occurred. If desired, such markers or other inserted sequences can later be removed by, e.g., Cre-Lox or similar systems.

Targeted gene modification uses nucleic acid constructs which have regions of homology with a target gene (e.g., SIGLEC1 or CD163) or with the flanking regions of a target gene, such that integration of the construct into the genome alters expression of the gene, either by changing the sequence of the gene and/or by altering the levels of expression of the gene. Thus, to alter a gene, a targeting construct is generally designed to contain three main regions: (i) a first region that is homologous to the locus to be targeted (e.g., the SIGLEC1 or CD163 gene, or a flanking sequence thereof), (ii) a second region that is a heterologous polynucleotide sequence (e.g., encoding a selectable marker, such as an antibiotic resistance protein) that is to specifically replace a portion of the targeted locus or is inserted into the targeted locus, and (iii) a third region that, like the first region, is homologous to the targeted locus, but typically is not contiguous with the first region of the construct. Homologous recombination between the targeting construct and the targeted wild-type locus results in deletion of any locus sequences between the two regions of homology represented in the targeting vector and replacement of that sequence with, or insertion into that sequence of, a heterologous sequence (e.g., a heterologous sequence that encodes a selectable marker). An exemplary construct and vector for carrying out such targeted modification is described in Example 1; however, other vectors that can be used in such approaches are known in the art and can readily be adapted for use in the invention.

In order to facilitate homologous recombination, the first and third regions of the targeting vectors (see above) include sequences that exhibit substantial sequence identity to the genes to be targeted (or flanking regions). For example, the first and third regions of the targeting vectors can have sequences that are at least about 80%, at least about 90%, at least about 95%, at least about 98%, at least about 99%, or about 100% identical to the targeted genes or flanking regions. Sequence identity is typically measured using BLAST® (Basic Local Alignment Search Tool) or BLAST® 2 with the default parameters specified therein (see, Altschul et al., J. Mol. Biol. 215:403-410, 1990; Tatiana et al., FEMS Microbiol. Lett. 174:247-250, 1999). Thus, sequences having at least about 80%, at least about 90%, at least about 95%, at least about 98%, at least about 99%, or even about 100% sequence identity with the targeted gene loci can be used in the invention to facilitate homologous recombination.

The total size of the two regions of homology (i.e., the first and third regions described above) can be, for example, about 2 kilobases (kb) to about 25 kb (e.g., about 4 kb to about 20 kb, about 5 kb to about 15 kb, or about 6 kb to about 10 kb). The size of the region that replaces a portion of the targeted locus or is inserted into the targeted locus (the second region as described above) can be, for example, about 0.5 kb to about 5 kb (e.g., about 1 kb to about 4 kb or about 3 to about 4 kb).

Various types of targeting construct delivery methods can be used. Cell transfection methods, including calcium phosphate, lipofection, electroporation, and nuclear injection can be used to deliver the targeting construct. If the gene is transcriptionally active in the cell type being used, then a promoterless selectable marker strategy can be employed, so that antibiotic resistance will only be found in cells that have had a recombination event within a transcribed unit. Alternatively, if the gene is transcriptionally inactive in the cell type being used, promoters that are inducible, tissue-specific or contain insulators such as matrix attachment regions (MARs) can be used.

Alternatively, siRNA technology can be used to "silence" the transcript for SIGLEC1. Antisense technology is well known in the art. Briefly, a nucleotide sequence generally containing between about 19 and about 29 nucleotides which is complementary to the sense mRNA sequence of SIGLEC1 is used. The degree of complementarity generally ranges from about 70% to about 100%. Preferably, complementarity is greater than about 80%, more preferably greater than about 90%, and even more preferably greater than about 95%. Regions of SIGLEC1 mRNA that are suitable for targeting with siRNA can be readily determined by comparing the efficacy of several antisense sequences designed to be complementary to different regions of SIGLEC1 mRNA in preventing production of the SIGLEC1 protein. Such experiments can be readily performed without undue experimentation by any of the known techniques in the art.

Vectors used for siRNA expression are well known in the art. The vector may be any circular or linear length of DNA that either integrates into the host genome or is maintained in episomal form. In general, siRNA expression cassettes may be ligated into a DNA transfer vector, such as a plasmid, or a lentiviral, adenoviral, alphaviral, retroviral or other viral vector. Exemplary mammalian viral vector systems include adenoviral vectors; adeno-associated type 1 ("AAV-1") or adeno-associated type 2 ("AAV-2") viral vectors; hepatitis delta vectors; live, attenuated delta viruses; herpes viral vectors; alphaviral vectors; or retroviral vectors (including lentiviral vectors).

Transformation of mammalian cells can be performed according to standard techniques known in the art. Any of the well-known procedures for introducing foreign nucleotide sequences into host cells can be used so long as they successfully introduce at least the siRNA construct into the host cell. These procedures include the use of viral transduction (for example, by use of any of the viral vectors listed in the preceding paragraph, e.g., by retroviral infection, optionally in the presence of polybrene to enhance infection efficiency), calcium phosphate transfection, electroporation, biolistic particle delivery system (i.e., gene guns), liposomes, microinjection, and any of the other known methods for introducing cloned genomic DNA, cDNA, synthetic DNA or other foreign genetic material into a host cell. In the present invention, the siRNA directed against SIGLEC1 is introduced into a donor swine fibroblast cell, which is subsequently used to produce a transgenically modified swine of the present invention.

The transgenic animals of the invention can be made using the following general somatic cell nuclear transfer procedure. Briefly, the genome of a somatic porcine cell (e.g., a fetal fibroblast) is genetically modified by gene targeting as described above, to create a donor cell. The nucleus of such a genetically modified donor cell (or the entire donor cell, including the nucleus) is then transferred into a recipient cell, for example, an enucleated oocyte. The donor cell can be fused with a enucleated oocyte, or donor nucleus or the donor cell itself can be injected into the recipient cell or injected into the perivitelline space, adjacent to the oocyte membrane.

Thus, upon obtaining somatic cells in which a target gene has been targeted (one or both alleles, as described above), nuclear transfer can be carried out. Optionally, the genetically modified donor cells can be cryopreserved prior to nuclear transfer. Recipient cells that can be used include oocytes, fertilized zygotes, or the cells of two-cell embryos, all of which may or may not have been enucleated.

Recipient oocytes can be obtained using methods that are known in the art or can be purchased from commercial sources (e.g., BoMed Inc., Madison, Wis.). The oocyte can be obtained from a "gilt," a female pig that has never had offspring or from a "sow," a female pig that has previously produced offspring.

Accordingly, a genetically modified swine wherein at least one allele of a SIGLEC1 gene has been inactivated can be produced by enucleating a swine oocyte; fusing the oocyte with a donor swine fibroblast cell, the genome of the fibroblast cell comprising at least one inactivated SIGLEC1 allele; and activating the oocyte to produce an embryo. Similarly, a genetically modified swine wherein at least one allele of a CD163 gene has been inactivated, wherein inactivation of the CD163 allele results in a CD163 protein which cannot bind and/or uncoat a porcine reproductive and respiratory syndrome virus (PRRSV) can be produced by enucleating a swine oocyte; fusing the oocyte with a donor swine fibroblast cell, the genome of the fibroblast cell comprising at least one inactivated CD163 allele; and activating the oocyte to produce an embryo. Both methods can further include a step of transferring the embryo into a reproductive tract of a surrogate swine, wherein the surrogate swine has initiated estrus but has not yet completed ovulation; and wherein gestation and term delivery of the embryo produces a genetically modified swine whose genome comprises at least one inactivated SIGLEC1 and/or CD163 allele. The present invention also relates to progeny of such genetically modified swine wherein at least one allele of a SIGLEC1 gene has been inactivated and/or wherein at least one allele of a CD163 gene has been inactivated, wherein inactivation of the CD163 allele results in a CD163 protein which cannot bind and/or uncoat a porcine reproductive and respiratory syndrome virus (PRRSV).

Methods for enucleating swine oocytes are known in the art, and enucleation can be achieved by any of the standard methods. For example, enucleating a oocyte can be achieved with a micropipette in a micromanipulation medium.

Introduction of a membrane-bound nucleus from a donor swine cell into an enucleated recipient swine oocyte to form an oocyte containing the donor nucleus can be performed by fusing together the membrane of the membrane-bound nucleus from the donor mammalian cell with the membrane of the enucleated recipient mammalian oocyte to form an oocyte containing the nucleus from the donor mammalian cell. Alternatively, such introduction can be performed by microinjecting the membrane-bounded nucleus from the mammalian donor cell into the enucleated recipient mammalian oocyte to form an oocyte containing the nucleus from the donor mammalian cell. For example, one can introduce a donor cell (or nucleus) into the space under the zona pellucida or into the perivitelline space of the enucleated, recipient oocyte, and subsequently carry out membrane fusion to produce an oocyte containing within its cytoplasm the donor nucleus. All means of introducing donor nuclear material into an enucleated recipient mammalian oocyte known to those of ordinary skill in the art are useful in the methods disclosed herein.

For example, the fusing step can be performed in a fusion medium. Alternatively, an inactivated virus or a fuseogenic agent such as polyethylene glycol (PEG) can be used to promote fusion. See, e.g., Graham (1969) Wistar Inst. Symp. Monogr. 9:19-33, and McGrath et al. (1983) Science 220: 1300-1302 for the use of viruses; Fisher et al. (1981) Tech. Cell. Physiol. 1:1-36 for chemically induced cell fusion; and Berg (1982) Bioelectrochem. Bioenerg. 9:223-228, and Robl et al. (1987) J. Anim. Sci. 64:642-647 for electrically induced cell fusion.

U.S. Pat. No. 6,211,429 B1, the contents of which are hereby incorporated by reference, describes methods for in vitro and in vivo development of activated oocytes. The term "activated" or "activation" refers to the capacity of an unfertilized oocyte to develop to at least the pronuclear stage, or beyond, after treatment with an oocyte-modifying agent and a reducing agent. Generally speaking, the pronuclear stage is achieved about three to seven hours after such treatment. The term "oocyte-modifying agent" refers to an agent that can react with a substrate on or in an oocyte, for example a thiol (—SH) group, which can be a protein thiol group; the effect of this reaction, when followed by treatment of the oocyte with a reducing agent according to the methods disclosed in U.S. Pat. No. 6,211,429 B1, results in activation of mammalian oocytes.

The combined use of an —SH or oocyte-modifying agent such as thimerosal and an —SH reducing agent such as dithiothreitol is able to induce complete activation of mammalian oocytes. Coupling of a short treatment with thimerosal with only a single calcium transient before treatment with a reducing agent such as DTT is particularly effective in achieving activation. Thimerosal triggers a series of $Ca^{2+}$ spikes in mammalian oocytes, which when followed by an incubation with a reducing agent such as DTT can stimulate pronuclear formation. Thus, after thimerosal is washed out, DTT is then added to reverse the actions of thimerosal, followed by washing it out to allow the embryo to continue development. The combined thimerosal/DTT treatment also induces cortical granule exocytosis, subsequent hardening of the zona pellucida, and development of the activated oocytes to the blastocyst stage.

In addition to thimerosal, other oocyte-modifying agents can be used, such as t-butyl hydroperoxide; thiourea; phenylephrine; N-aklylmaleimides such as N-ethylmaleimide; oxidized glutathione; alpha-haloacids such as iodoacetate, chloroacetate, and bromoacetate; iodoacetamide; p-mercuribenzoate; p-chloromercuribenzoate; 5,5'-dithiobis(2-nitrobenzoic acid) (DTNB); (2-trimethylammonium)ethylmethanethiosulfonate (MTSET); and (2-sulfonatoethyl)methanethiosulfonate (MTSES). Useful reducing agents, such as thiol (—SH) group reducing agents, in addition to DTT, include but are not limited to dithioerythritol (DTE); beta-mercaptoethanol; cysteine; reduced glutathione; reduced thiourea; thioglycolate; and ascorbic acid.

The time period during which oocytes are contacted with the oocyte-modifying agent is a period effective to result in activation of the oocytes when followed by treatment with a reducing agent. Such time period can be in the range of from about 5 minutes to about 20 minutes, preferably from about 5 minutes to about 15 minutes, or more preferably from about 5 minutes to about 12 minutes. The time period during which the oocytes are contacted with the reducing agent is suitably long enough to result in activation of the oocytes when preceded by treatment with an oocyte-modifying agent. Such time period can be in the range of from about 5 minutes to about 1 hour, preferably from about 10 minutes to about 45 minutes, more preferably from about 20 minutes to about 40 minutes, and still more preferably about 30 minutes.

Contacting of the enucleated oocyte with the reducing agent following the contacting with the oocyte-modifying agent can occur substantially immediately, or can occur within a time interval in the range of from about 5 seconds to about 5 minutes after exposure of the oocyte to the oocyte-modifying agent. The oocyte-modifying agent-treated oocyte can be transferred into medium containing the reducing agent without any intermediate wash step. Alternatively, the oocyte-modifying agent-treated oocyte can be washed in control or reducing agent-containing medium to substantially remove oocyte-modifying agent before culturing the oocyte in reducing agent-containing medium. As another alternative, the reducing agent can be added directly to the oocyte while the latter is still present in oocyte-modifying agent-containing medium.

Alternatively, oocyte activation can also be achieved with a number of other chemical treatments that do not involve calcium, e.g., protein kinase inhibition (Mayes et al. (1995) Biol. Reprod. 53:270-275), or inhibition of protein synthesis (Nussbaum et al. (1995) Mol. Reprod. Dev. 41:70-75).

After activation, the oocyte is typically cultured for a brief period in vitro. The resulting embryo is then transferred into a surrogate female, and development of the embryo proceeds in the surrogate. For example, the embryos can be cultured for about a week, and then transferred surgically or non-surgically to the reproductive tract of a surrogate. The embryos can be transferred into an oviduct through an ovarian fimbria of the surrogate. Alternatively, the embryos can be transferred into an oviduct of a surrogate by using a catheter that penetrates the wall of the oviduct. Another way of transferring embryos involves culturing them until the blastocyst stage followed by introduction into the reproductive tract of a surrogate swine. These methods are well known in the art, and can readily be applied in producing the genetically modified swine of the present invention.

Additional methods for making genetically modified swine and other large animals are known in the art and can also be used in the present invention (see, e.g., US 2005/0120400 A1; U.S. Pat. No. 5,945,577; WO 96/07732; WO 97/07669; WO 97/07668; WO 2005/104835; Lai et al., Reproductive Biology and Endocrinology 1:82, 2003; Hao et al., Transgenic Res. 15:739-750, 2006; Li et al., Biology of Reproduction 75:226-230, 2006; Lai et al., Nature Biotechnology 24(4):435-436, 2006; Lai et al., Methods in Molecular Biology 254(2):149-163, 2004; Lai et al., Cloning and Stem Cells 5(4):233-241, 2003; Park et al., Animal Biotechnology 12(2):173-181, 2001; Lai et al., Science 295:1089-1092, 2002; Park et al., Biology of Reproduction 65:1681-1685, 2001; the contents of each of which are incorporated herein by reference).

Other feasible methods for producing genetically modified swine include injection or transduction of nucleases (zinc-finger nucleases, or Tal nucleases that would target the gene of interest) into somatic cells, followed by somatic cell nuclear transfer and transfer of the embryo into a surrogate. In addition, sperm- or intracytoplasmic sperm injection (ICSI)-mediated genetic modification can also be employed. Briefly, in ICSI-mediated modification, a targeting construct is mixed with the sperm, and both are injected into an oocyte. In sperm-mediated modification, the construct is mixed with the sperm, and in vitro fertilization (IVF) or insemination is used to impregnate a surrogate. A skilled artisan can readily adjust these methods to production of knockout pigs of the present invention. While not fully developed for the pig, embryonic stem cell technology, or induced pluripotent cells, as have been developed for mouse, may be genetically modified and used either as donor cells for somatic cell nuclear transfer or for the production of chimeric animals.

As mentioned above, the present invention is also directed to genetically modified swine in which (1) both alleles of SIGLEC1 gene have been inactivated, (2) both alleles of CD163 genes have been inactivated, wherein inactivation of the CD163 alleles results in a CD163 protein which cannot bind and/or uncoat a porcine reproductive and respiratory syndrome virus (PRRSV), or (3) both alleles of SIGLEC1 and both alleles of CD163 have been inactivated. Genetically modified swine which are homozygous for gene inactivation can be produced by mating swine heterozygous for gene inactivation, and screening the progeny to identify animals which are homozygous for inactivation of the gene(s). The present invention is also directed to progeny of such genetically modified swine, wherein one or both alleles of a SIGLEC1 gene have been inactivated and/or wherein one or both alleles of a CD163 gene have been inactivated, wherein inactivation of the CD163 alleles results in a CD163 protein which cannot bind and/or uncoat a porcine reproductive and respiratory syndrome virus (PRRSV).

Accordingly, the present invention is directed to a method for producing a genetically modified swine wherein both alleles of a SIGLEC1 gene have been inactivated by mating a female genetically modified swine wherein at least one allele of a SIGLEC1 has been inactivated with a male genetically modified swine wherein at least one allele of SIGLEC1 has been inactivated to produce F1 progeny; and screening the F1 progeny to identify genetically modified swine wherein both alleles of the SIGLEC1 gene have been inactivated. Similarly, the present invention is directed to a method for producing a genetically modified swine wherein both alleles of a CD163 gene have been inactivated by mating a female genetically modified swine wherein at least one allele of CD163 has been inactivated with a male genetically modified swine wherein at least one allele of CD163 has been inactivated to produce F1 progeny; and screening the F1 progeny to identify genetically modified swine wherein both alleles of the CD163 gene have been inactivated.

The present invention also provides methods for producing a genetically modified swine wherein both alleles of a SIGLEC1 gene and both alleles of a CD163 gene have been inactivated. One such method comprises mating a genetically modified swine wherein at least one allele of a SIGLEC1 gene has been inactivated with a genetically modified swine wherein at least one allele of a CD163 gene has been inactivated to produce F1 progeny; screening the F1 progeny to identify genetically modified swine wherein at least one allele of the SIGLEC1 gene has been inactivated and at least one allele of the CD163 gene has been inactivated; mating the genetically modified swine wherein at least one allele of the SIGLEC1 gene has been inactivated and at least one allele of the CD163 gene has been inactivated to each other produce F2 progeny; and screening the F2 progeny to identify genetically modified swine wherein both alleles of the SIGLEC1 gene and both alleles of the CD163 gene have been inactivated.

Methods for producing genetically modified swine wherein at least one allele of a SIGLEC1 and/or at least one allele of a CD163 gene have been inactivated are disclosed in the foregoing sections. Screening of progeny can be performed as is standard in the art, e.g., by using PCR or Southern blotting.

Another method for producing a genetically modified swine wherein both alleles of a SIGLEC1 gene and both alleles of a CD163 gene have been inactivated comprises mating a genetically modified swine homozygous for SIGLEC1 inactivation with a genetically modified swine homozygous for CD163 inactivation to produce F1 progeny, mating the F1 progeny to generate F2 progeny, and screening the F2 progeny to identify animals homozygous for both SIGLEC1 and CD163 inactivation.

Yet another method for producing a genetically modified swine wherein both alleles of a SIGLEC1 gene and both alleles of a CD163 gene have been inactivated comprises mating a genetically modified swine wherein at least one allele of a SIGLEC1 gene and at least one allele of a CD163 gene have been inactivated to another genetically modified swine wherein at least one allele of a SIGLEC1 gene and at least one allele of a CD163 gene have been inactivated to produce F1 progeny; and screening the F1 progeny to identify genetically modified swine wherein both alleles of the SIGLEC1 gene and both alleles of the CD163 gene have been inactivated.

The present invention also relates to progeny of genetically modified swine produced by any of the methods above, wherein one or both alleles of a SIGLEC1 gene have been inactivated and/or wherein one or both alleles of a CD163 gene have been inactivated, wherein inactivation of the CD163 gene results in a CD163 protein which cannot bind and/or uncoat a porcine reproductive and respiratory syndrome virus (PRRSV).

In addition to being obtainable by breeding approaches involving heterozygous animals, homozygous mutant animals can also be obtained using an approach in which a cell (e.g., a fetal fibroblast) including a mutation in one allele, such as a cell obtained from an animal produced using the method summarized above, is subjected to gene targeting by homologous recombination to achieve modification of the remaining allele. The resulting donor cell can then be used as a source of a modified nucleus for nuclear transfer into a recipient cell, such as an enucleated oocyte, leading to the formation of a homozygous mutant embryo which, when implanted into a surrogate female, develops into a homozygous mutant animal. Genetically modified swine wherein both alleles of SIGLEC1 and/or cD163 gene(s) have been inactivated can also be produced by injecting or transducing zinc finger nucleases or Tal nucleases (which can target both alleles of a gene at the same time) into somatic cells, followed by somatic cell nuclear transfer (SCNT) and embryo transfer into a surrogate to produce such swine. The present invention also relates to progeny of such genetically modified swine, wherein one or both alleles of a SIGLEC1 gene have been inactivated and/or wherein one or both alleles of a CD163 gene have been inactivated, wherein inactivation of the CD163 gene results in a CD163 protein which cannot bind and/or uncoat a porcine reproductive and respiratory syndrome virus (PRRSV).

Having described the invention in detail, it will be apparent that modifications and variations are possible without departing from the scope of the invention defined in the appended claims.

EXAMPLES

The following non-limiting examples are provided to further illustrate the present invention.

Example 1

Modification of the SIGLEC1 Gene

The approach employed to ablate the sialoadhesin gene made use of homologous recombination to remove protein coding exons and introduce premature stops in the remaining coding sequence of the sialoadhesin gene. The porcine sialoadhesin gene (SIGLEC1, NCBI reference sequence NM_214346) encodes a 210-kDa protein from an mRNA transcript of 5,193 bases (Vanderheij den et al. 2003). Porcine genomic sequence from the region around the sialoadhesin gene (Genbank accession no. CU467609) was used to generate oligonucleotides to amplify genomic fragments by high-fidelity PCR [AccuTaq (Invitrogen)] for generation of a targeting construct. One fragment (the 'upper arm') included the first coding exon and the 3304 bp upstream from the translation start. The second (lower arm') fragment was 4753 bp in length and included most of the intron downstream of the third coding exon and extended into the 6th intron (including the 4th, 5th and 6th coding exons). Based on comparisons with the mouse and human sialoadhesin genomic sequences, the porcine sialoadhesin gene was predicted to be composed of 21 exons (panels A and B of FIG. 1). Exon 2 is conserved between pig, mouse, and human. An amino acid alignment of exon 2 revealed that the six amino acids in mouse sialoadhesin known to be associated with sialic acid binding activity were conserved in pig sialoadhesin (panel C of FIG. 1). The initial targeting strategy focused on creating alterations in the sialoadhesion gene such that no functional protein was expected to be obtained from the mutated gene. Other inactivation strategies could include targeted modification of selected residues in exon 2 of the sialoadehesin gene or altering the immunoglobulin domains in ways predicted to preclude PRRS virus binding (possibly by changing their order or by substituting them for comparable domains from other species). Additional modifications may include flanking of the neomycin cassette or one of the immunoglobulin-like domains with loxP sites to permit inducible or tissue-specific removal if desirable.

In the current gene disruption, part of exon 1 and all of exons 2 and 3 were replaced with a neomycin selectable cassette by using a replacement-type vector (panel D of FIG. 1) (Mansour et al. 1988). In the plasmid construct, the phosphoglycerol kinase (PGK) promoter was used to drive expression of the neomycin cassette to permit positive selection of transfected colonies.

Donor Cell Preparation

A male fetal fibroblast primary cell line, from day 35 of gestation, was isolated from large commercial white pigs (Landrace). The cells were cultured and grown for 48 hours to 80% confluence in Dulbeco's Modified Eagles Medium (DMEM) containing 5 mM glutamine, sodium bicarbonate (3.7 g/L), penicillin-streptomycin and 1 g/L d-glucose, and supplemented with 15% Hyclone's Fetal bovine Serum, 10 µg/ml gentamicin, and 2.5 ng/ml basic fibroblast growth factor (Sigma). The media was removed and replaced with fresh media four hours prior to the transfection. Fibroblast cells were washed with 10 mls of phosphate buffered saline (DPBS; Invitrogen) and lifted off the 75 cm² flask with 1 ml of 0.05% trypsin-EDTA (Invitrogen). The cells were resuspended in DMEM and collected by centrifugation at 600×g for 10 mins. The cells were washed with Opti-MEM (Invitrogen) and centrifuged again at 600×g for 10 minutes. Cytosalts (75% cytosalts [120 mM KCl, 0.15 mM CaCl$_2$, 10 mM K$_2$HPO$_4$; pH 7.6, 5 mM MgCl$_2$]) and 25% Opti-Mem were used to resuspend the pellet (van den Hoff et al. 1992). The cells were counted with a hemocytometer and adjusted to 1×10$^6$ cells per ml. Electroporation of the cells was performed with 4 µg of single stranded targeting DNA (achieved by heat denaturation) in 200 µl of transfection media consisting of 1×10$^6$ cells/ml. The cells were electroporated in a BTX ECM 2001 electro cell manipulator by using three 1 msec pulses of 250V. The electroporated cells were diluted in DMEM/FBS/FGF at 10,000 cells per 13 cm plate. The electroporated cells were cultured overnight without selective pressure. The following day, media was replaced with culture media containing G418 (0.6 mg/ml). After 10 days of selection, G418-resistant colonies were isolated and transferred to 24-well plates for expansion. After growth in the 24-well plates, the cells were split (~half were used for genomic DNA isolation) into 6-well plates. PCR was used to determine if targeting of the sialoadhesin gene was successful. The reaction used oligonucleotides that annealed in the phosphoglucokinase (PGK) cassette (which includes Neo) paired with the ones that annealed to genomic DNA in the sialoadhesin locus that was beyond the region of the targeting arms (see FIG. 2). Successful targeting of both 'arms' was assessed in this way. A targeted fibroblast clone (4-18) was identified and some of the cells in the culture were used for nuclear transfer (see below) while others were frozen for future use. Southern blot verification of homologous recombination was used to provide additional confirmation of successful targeting.

Collection of Oocytes and In Vitro Maturation (IVM)

Pig oocytes were purchased from ART Inc (Madison, Wis.) and matured according to the supplier's instructions. After 42-44 h of in vitro maturation, the oocytes were stripped of their cumulus cells by gentle vortexing in 0.5 mg/ml hyaluronidase. After removal of the cumulus cells, oocytes with good morphology and a visible polar body (metaphase II) were selected and kept in the micromanipulation medium at 38.5° C. until nuclear transfer.

Somatic Cell Nuclear Transfer, Fusion/Activation of Nuclear Transfer Complex Oocytes, and In Vitro Developmental Culture Under a microscope, a cumulus-free oocyte was held with a holding micropipette in drops of micromanipulation medium supplemented with 7.5 µg/mL cytochalasin B and covered with mineral oil. The zona pellucida was penetrated with a fine glass injecting micropipette near the first polar body, and the first polar body and adjacent cytoplasm, presumably containing the metaphase-II chromosomes, was aspirated into the pipette, the pipette was withdrawn and the contents discarded. A single, round, and bright donor cell with a smooth surface was selected and transferred into the perivitelline space adjacent to the oocyte membrane (Lai et al. 2006; Lai et al. 2002).

The nuclear transfer complex (oocyte+fibroblast) was fused in fusion medium with a low calcium concentration (0.3 M mannitol, 0.1 mM CaCl$_2$.2H$_2$O, 0.1 mM MgCl$_2$.6H$_2$O and 0.5 mM HEPES). The fused oocytes were then activated by treatment with 200 µM thimerosal for 10 minutes in the dark, followed by rinsing and treatment with 8 mM dithiothreitol (DTT) for 30 minutes; the oocytes were then rinsed again to remove the DTT (Macháty and Prather 2001; Machaty et al. 1997). Following fusion/activation, the oocytes were washed three times with porcine zygote medium 3 (PZM3) supplemented with 4 mg/mL of BSA (Im et al. 2004), and cultured at 38.5° C. in a humidified atmosphere of 5% $O_2$, 90% $N_2$ and 5% $CO_2$ for 30 min. Those complexes that had successfully fused were cultured for 15-21 hours until surgical embryo transfer to a surrogate.

Surrogate Preparation, Embryo Transfer, Pregnancy Diagnosis and Delivery

The surrogate gilts were synchronized by administering 18-20 mg REGU-MATE (altrenogest 0.22% solution) (Intervet, Millsboro, Del.) mixed into the feed for 14 days using a scheme dependent on the stage of the estrous cycle. After the last REGU-MATE treatment (105 hours), an IM injection of 1000 units of hCG was given to induce estrus. Other surrogates that had naturally cycled on the appropriate date were also included in the surrogate pool. Surrogates on the day of (day 0), or the first day after, standing estrus were used (Lai et al. 2002). The surrogates were aseptically prepared and a caudal ventral incision was made to expose the reproductive tract. Embryos were transferred into one oviduct through the ovarian fimbria. Surrogates were checked for pregnancy by abdominal ultrasound examination around day 30, and then checked once a week through gestation. Parturition is in the pig is generally at 114 days of gestation.

After transfection and screening of fetal fibroblast cells candidate donor cells were identified and used for somatic cell nuclear transfer (SCNT). Six hundred and sixty-six SCNT embryos were transferred to two surrogates. One delivered 6 normal male piglets on day 115 of gestation, and a C-section was performed on the other surrogate on day 117 of gestation resulting in two normal male piglets, as show in Table 1.

ID NOs: 2 and 5, respectively)). There is approximately a 500 bp difference in product size between the disrupted allele and the wild-type allele.

TABLE 2

Primer names and sequences used in the project.

| | |
|---|---|
| upper sialo targeting C | ggaacaggctgagccaataa (SEQ ID NO: 1) |
| Exon 1 end ck | gcattcctaggcacagc (SEQ ID NO: 2) |
| PGK polyA reverse | ggttctaagtactgtggtttcc (SEQ ID NO: 3) |
| PGK promoter forward | agaggccacttgtgtagcgc (SEQ ID NO: 4) |
| Intron 3 ck Reverse | ctccttgccatgtccag (SEQ ID NO. 5) |
| 7Rw1 | caggtaccaggaaaaacgggt (SEQ ID NO: 6) |

Figure 2:
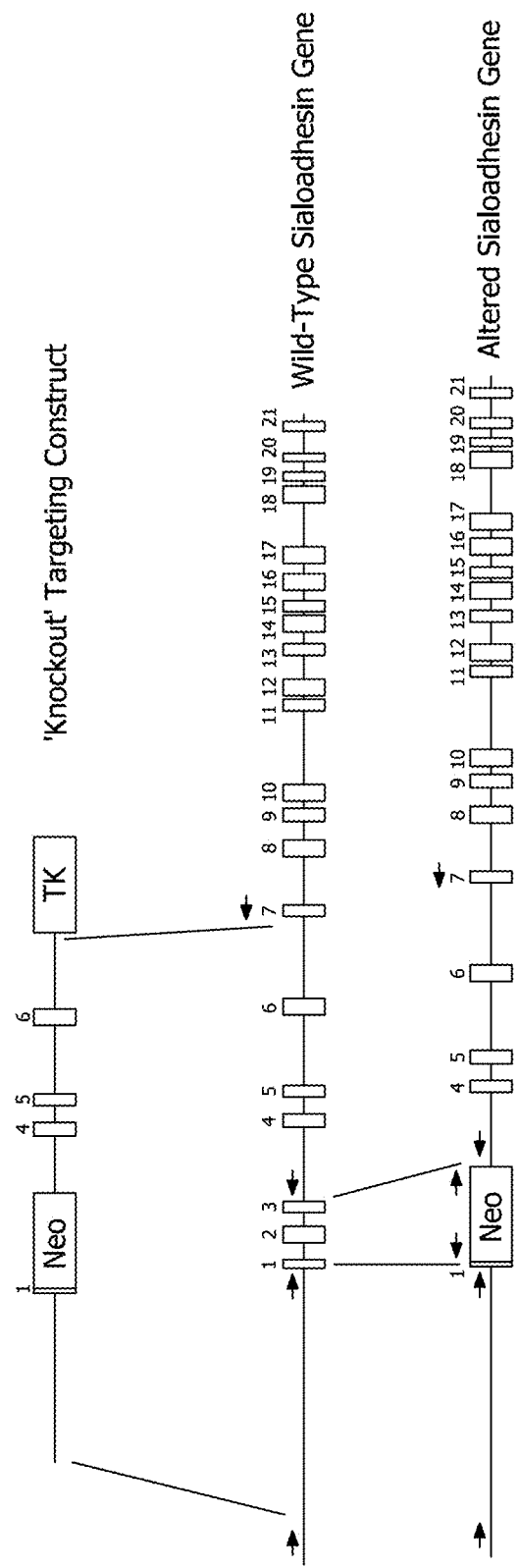
FIG. 2 depicts the targeting vector design, the organization of the sialoadhesin gene, and the organization of the altered sialoadhesin gene.

The primers in Table 2 were assigned sequence ID numbers based on the position of the arrows in the bottom panel of FIG. 2 going from left to right. Thus, the left-most arrow in the bottom panel of FIG. 2 shows the location of the "upper sialo targeting C" primer (SEQ ID NO: 1), the next arrow to the right shows the location of the "Exon 1 end ck" primer (SEQ ID NO: 2), the next arrow to the right of that shows the location of the "PGK polyA reverse" primer (SEQ ID NO: 3), and so forth.

TABLE 1

Embryo transfer results from using SIGLEC1 +/− male donor cells.

| Date | Surrogate | Genotype | # Transferred | Results |
|---|---|---|---|---|
| Sep. 23, 2010 | O963 | SIGLEC1+/− ♂ | 388 | 6 normal male piglets born Jan. 16, 2011 |
| Sep. 24, 2010 | O962 | SIGLEC1+/− ♂ | 278 | 2 normal male piglets delivered by C-section Jan. 18, 2011 |

Figure 3:
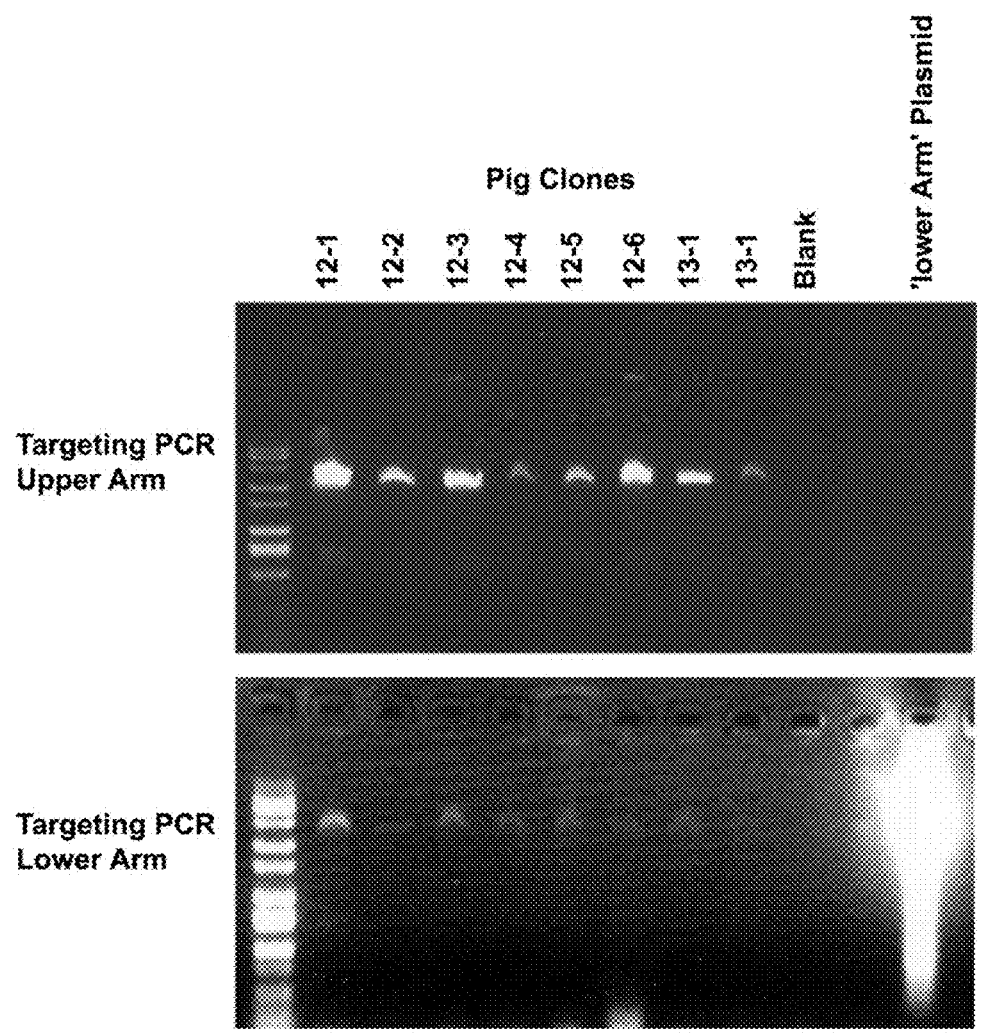
FIG. 3 is a photograph of a gel showing the PCR screening to identify targeting of the sialoadhesin gene.

FIG. 2 shows the organization of the sialoadhesin (SIGLEC1) gene, targeting vector and expected recombined genotype. The top panel of FIG. 2 shows the targeting construct used for homologous recombination. As described above, the 'upper' DNA fragment used to create the targeting construct contained ~3.5 kb upstream of exon 1 and included part of exon 1 (after the start codon). The 'lower' DNA fragment began within intron 3 and included exons 4, 5, 6 and part of exon 7. Most of exon 1 and all of exons 2 & 3 were substituted with a neomycin (neo) cassette; a thymidine kinase (TK) cassette was available immediately downstream of the lower arm for use as a negative selectable marker if necessary. The bottom panel of FIG. 2 illustrates the mutated sialoadhesin gene following homologous recombination. The arrows represent oligonucleotide binding sites used for PCR-based screening of targeted cell lines and cloned pigs. Targeting by the upper and lower arms was performed by oligonucleotides annealing as shown by arrows representing primers "upper sialo targeting C" and "PGK polyA reverse" (SEQ ID NOs: 1 and 3) and "PGK promoter forward" and "7Rw1" (SEQ ID NOs: 4 and 6), respectively. The oligonucleotide sequences are listed in Table 2 below. An additional check PCR made use of oligonucleotides that flanked the ablated region/Neo cassette (primers "Exon 1 end ck" and "Intron 3 ck Reverse" (SEQ Screening for SIGLEC1 Inactivation Genomic DNA was isolated from the piglets and used to confirm the targeting events. Successful targeting of the SIGLEC1 gene was determined by using PCR with oligonucleotides that annealed within the Neo cassette paired with oligonucleotides that annealed to SIGLEC1 genomic DNA that was beyond the region contained within the targeting construct. In the top panel of FIG. 3, targeting by the 'upper' arm was examined by using the 'PGK polyA reverse' and 'upper sialo targeting C' oligonucleotides (SEQ ID NOs. 3 and 1, respectively; illustrated in FIG. 2). A product of the expected size (~4500 bp) was produced. In the bottom panel, successful targeting by the 'lower' arm was determined by using the 'PGK promoter forward' and '7Rw1' oligonucleotides (SEQ ID NOs: 4 and 6, respectively; illustrated in FIG. 2). A product of the expected size (~5000 bp) was produced. The 'lower arm plasmid' control was a partial construct containing the Neo cassette with a sialoadhesin gene fragment representing most of intron 3 and most of exon 7. The 7Rw1 oligonucleotide was able to anneal to the exon 7 sequence present in the plasmid, and along with the PGK promoter forward oligonucleotide, it was able to produce a product that was identical to what would be produced from a successful targeting event. Both panels illustrate targeting PCR reactions performed on genomic DNA extracted from eight piglet clones generated from the 4-18 targeted fetal fibroblast line.

Figure 4:
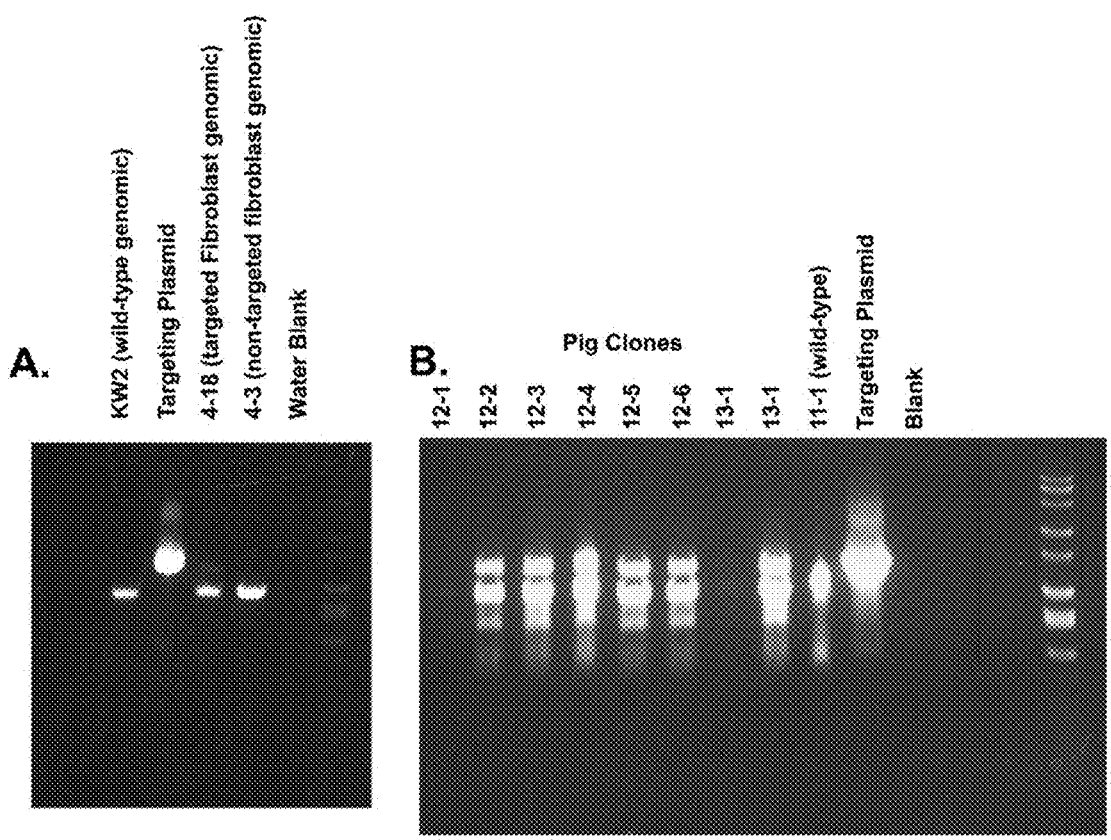
FIG. 4 is a photograph of a gel showing the PCR screening to identify the equal presence of both wild type and targeted sialoadhesin alleles.
Figure 5:
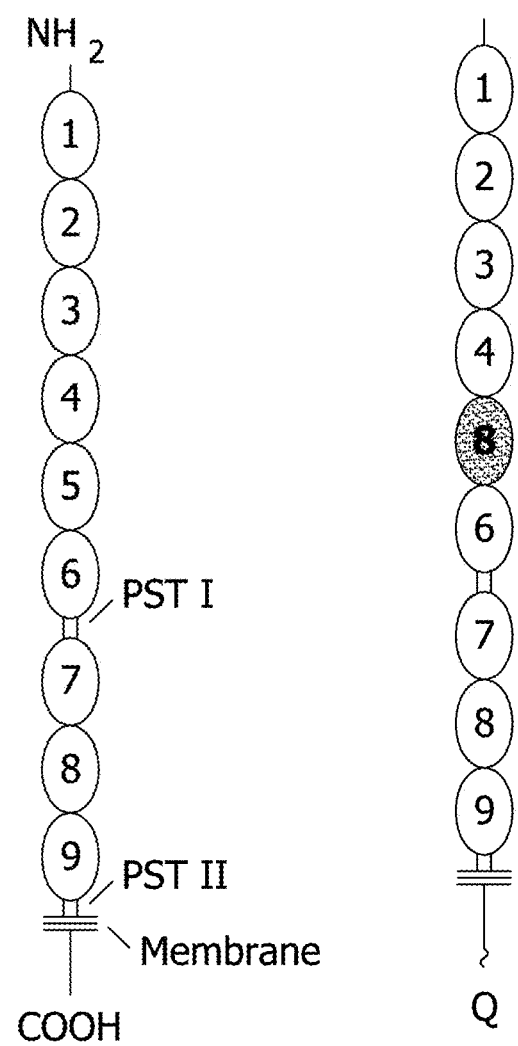
FIG. 5 depicts the structural domain organization of wild-type CD163 (on the left) containing 9 extracellular SRCR domains, 2 proline, serine, and threonine (PST)-rich domains, a transmembrane region and an intracellular cytoplasmic tail. The genetically modified CD163 is depicted on the right. The structural domain organization remains the same except that the SRCR domain 5 has been replaced with SRCR domain 8 from CD163 ligand (CD163L).

Detection of both wild-type and targeted sialoadhesin alleles was performed by using PCR with oligonucleotides that annealed to DNA flanking the targeted region of the sialoadhesin gene. The 'Exon 1 end ck' and 'Intron 3 ck Reverse' oligonucleotides were used (SEQ ID NOs: 2 and 5, respectively; illustrated in FIG. 2). The products generated were ~2400 bp for the wildtype allele and 2900 bp for the targeted allele. In FIG. 4, the panel on the left (panel A of FIG. 4) illustrates test reactions performed on wild-type genomic DNA, the targeting plasmid used for transfections, genomic DNA (4-18) from a successfully targeted fibroblast clone (note the two bands) and genomic DNA (4-3) from a non-targeted fibroblast clone. The panel on the right (panel B of FIG. 4) illustrates the reaction performed on genomic DNA extracted from eight piglet clones generated from the 4-18 targeted fetal fibroblast line. There were two PCR products of the expected sizes in each lane, while the wildtype DNA and targeting plasmid templates only had a single band. Thus, all of the piglets produced by SCNT were heterozygous for the intended mutation, i.e. SIGLEC+/−.

Production of Homozygous Animals

Male genetically modified swine, which were identified as heterozygous for SIGLEC1 inactivation were used as male founders (F0 generation), and were mated to wild-type females to produce male and female animals that had one inactivated SIGLEC1 allele (F1). The F1 males were then mated to the F1 females to produce F2 progeny, which have both SIGLEC1 alleles inactivated. Such animals can be identified following birth by the PCR described above for SIGLEC1 or alternatively by Southern blotting.

Example 2

Generation of a CD163 Targeting Construct

Figure 6:
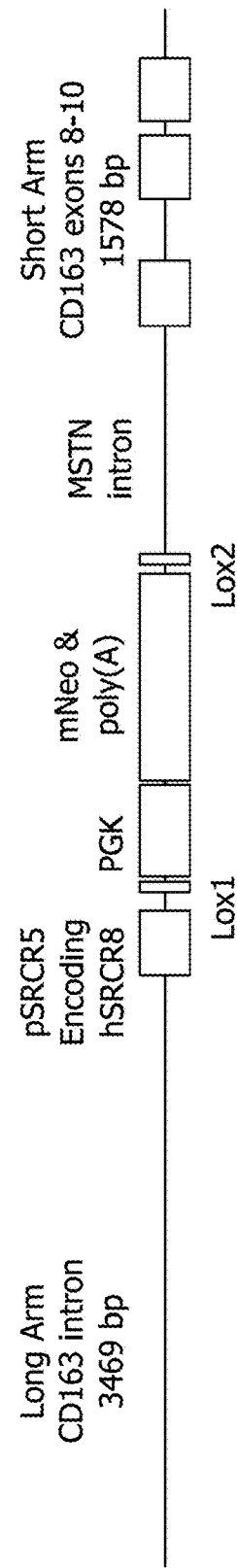
FIG. 6 depicts the CD163 targeting vector, wherein the arms of the vector are sections of DNA that have an identical sequence with the naturally occurring or wild-type CD163, thus allowing the vector to anneal to the CD163 already present in the cells. The modified DNA that lies between the two arms of CD163 can then be inserted into the cells' DNA by homologous recombination.

As already established, deletion of the cytoplasmic domain of CD163 eliminates infectivity of PRRSV, as does the deletion or modification of SRCR domain 5. Since some of the SRCR domains of CD163 have important functions for survival of the animal, e.g. hemoglobin removal, modification of the gene such that these other functions remain intact represents a solid strategy to create pigs that are resistant to PRRSV. Prior research has also suggested that the replacement of SRCRS domain with CD163L domain 8 also blocks infectivity (Van Gorp et al. 2010b). Thus, a targeting construct can be designed as shown in FIG. 6 to swap out SRCRS of CD163 with the SRCR domain CD163L.

Once the targeting construct is made, the genetically modified swine which are heterozygous for inactivated CD163, wherein inactivation of the CD163 gene results in a CD163 protein which cannot bind and/or uncoat a porcine reproductive and respiratory syndrome virus (PRRSV) is can be produced by methods which are generally the same as those described in Example 1. First, a targeting vector is inserted into a donor cell, where it can recombine with the endogenous CD163 gene. The donor cells with this specific modification are then selected and used for somatic cell nuclear transfer to create a genetically modified embryo. The embryo is then transferred to a surrogate for term gestation. After identifying transgenic swine with an inactivated CD163 allele by either PCR or Southern blotting, these animals are permitted to reach sexual maturity, and are then used for natural mating to transmit the gene to fetuses or offspring.

REFERENCES

Albina E, Madec F, Cariolet R, Torrison J. 1994. Immune Response and Persistence of the Porcine Reproductive and Respiratory Syndrome Virus in Infected Pigs and Farm Units. Veterinary Record 134(22):567-573.

Allende R, Laegreid W W, Kutish G F, Galeota J A, Wills R W, Osorio F A. 2000. Porcine reproductive and respiratory syndrome virus: Description of persistence in individual pigs upon experimental infection. Journal of Virology 74(22):10834-10837.

Andreyev V G, Wesley R D, Mengeling W L, Vorwald A C, Lager K M. 1997. Genetic Variation and Phylogenetic Relationships of 22 Porcine Reproductive and Respiratory Syndrome Virus (Prrsv) Field Strains Based on Sequence Analysis of Open Reading Frame 5. Archives of Virology 142(5):993-1001.

Benfield D A, Nelson E, Collins J E, Harris L, Goyal S M, Robison D, Christianson W T, Morrison R B, Gorcyca D, Chladek D. 1992. Characterization of swine infertility and respiratory syndrome (SIRS) virus (isolate ATCC VR-2332). Journal of Veterinary Diagnostic Investigation 4:127-133.

Benfield D A, Nelson J, Rossow K D, Rowland R R, Lawson S R, Steffen M, Collins M. 1998. Pathogenesis and persistence of PRRS. Proceedings, Allen D. Leman Swine Conference:169-171.

Christopherhennings J, Nelson E A, Hines R J, Nelson J K, Swenson S L, Zimmerman J J, Chase C C L, Yaeger M J, Benfield D A. 1995. Persistence of Porcine Reproductive and Respiratory Syndrome Virus in Serum and Semen of Adult Boars. Journal of Veterinary Diagnostic Investigation 7(4):456-464.

Christopherhennings J, Nelson E A, Nelson J K, Benfield D A. 1997. Effects of a Modified-Live Virus Vaccine against Porcine Reproductive and Respiratory Syndrome in Boars. American Journal of Veterinary Research 58(1): 40-45.

Crocker P R, Gordon S. 1986. Properties and distribution of a lectin-like hemagglutinin differentially expressed by murine stromal tissue macrophages. J Exp Med 164(6): 1862-1875.

Crocker P R, Vinson M, Kelm S, Drickamer K. 1999. Molecular analysis of sialoside binding to sialoadhesin by NMR and site-directed mutagenesis. Biochemical Journal 341(Part 2):355-361.

Das P B, Dinh P X, Ansari I H, de Lima M, Osorio F A, Pattnaik A K. 2010. The minor envelope glycoproteins GP2a and GP4 of porcine reproductive and respiratory syndrome virus interact with the receptor CD163. J Virol 84(4):1731-1740.

Dee S A, Molitor T W. 1998. Elimination of Porcine Reproductive and Respiratory Syndrome Virus Using a Test and Removal Process. Veterinary Record 143(17): 474-476.

Delputte P L, Meerts P, Costers S, Nauwynck H J. 2004. Effect of virus-specific antibodies on attachment, internalization and infection of porcine reproductive and respiratory syndrome virus in primary macrophages. Vet Immunol Immunopathol 102(3):179-188.

Delputte P L, Nauwynck H J. 2004. Porcine arterivirus infection of alveolar macrophages is mediated by sialic acid on the virus. Journal of Virology 78(15):8094-8101.

Delputte P L, Van Breedam W, Delrue I, Oetke C, Crocker P R, Nauwynck H J. 2007. Porcine arterivirus attachment to the macrophage-specific receptor sialoadhesin is dependent on the sialic acid-binding activity of the N-terminal immunoglobulin domain of sialoadhesin. J Virol 81(17):9546-9550.

Im G-S, Lai L, Liu Z, Hao Y, Prather R S. 2004. In vitro development of preimplantation porcine nuclear transfer embryos cultured in different media and gas atmospheres. Theriogenology 61:1125-1135.

Keffaber K K. 1989. Reproductive failure of unknown etiology. American Association of Swine Practitioners Newsletter 1:1-9.

Kristiansen M, Graversen J H, Jacobsen C, Sonne O, Hoffman H J, Law S K, Moestrup S K. 2001. Identification of the haemoglobin scavenger receptor. Nature 409(6817): 198-201.

Lager K M, Mengeling W L, Brockmeier S L. 1999. Evaluation of protective immunity in gilts inoculated with the NADC-8 isolate of porcine reproductive and respiratory syndrome virus (PRRSV) and challenge-exposed with an antigenically distinct PRRSV isolate. American Journal of Veterinary Research 60(8):1022-1027.

Lai L, Kang J X, Li R, Wang J, Witt W, Yong H Y, Hao Y, Wax D, Murphy C N, Rieke A, Samuel M, Linville M L, Korte S W, Evans R, Starzl T E, Prather R S, Dai Y. 2006. Generation of cloned transgenic pigs rich in omega-3 fatty acids. Nature Biotechnology 24:435-437.

Lai L X, Kolber-Simonds D, Park K W, Cheong H T, Greenstein J L, Im G S, Samuel M, Bonk A, Rieke A, Day B N, Murphy C N, Carter D B, Hawley R J, Prather R S. 2002. Production of alpha-1,3-galactosyltransferase knockout pigs by nuclear transfer cloning. Science 295 (5557): 1089-1092.

Macháty Z, Prather R S. 2001. Complete activation of mammalian oocytes. U S Patent Issued April 17: U.S. Pat. No. 6,211,429.

Machaty Z, Wang W H, Day B N, Prather R S. 1997. Complete Activation of Porcine Oocytes Induced by the Sulfhydryl Reagent, Thimerosal. Biology of Reproduction 57(5): 1123-1127.

Mansour S L, Thomas K R, Capecchi M R. 1988. Disruption of the proto-oncogene int-2 in mouse embryo-derived stem cells: a general strategy for targeting mutations to non-selectable genes. Nature 336:348-352.

Meng X J. 2000. Heterogeneity of porcine reproductive and respiratory syndrome virus: implications for current vaccine efficacy and future vaccine development [Review]. Veterinary Microbiology 74(4):309-329.

Meng X J, Paul P S, Halbur P G, Morozov I. 1995. Sequence Comparison of Open Reading Frames 2 to 5 of Low and High Virulence United States Isolates of Porcine Reproductive and Respiratory Syndrome Virus. Journal of General Virology 76(Part 12):3181-3188.

Mengeling W L, Vorwald A C, Lager K M, Clouser D F, Wesley R D. 1999. Identification and clinical assessment of suspected vaccine-related field strains of porcine reproductive and respiratory syndrome virus. American Journal of Veterinary Research 60(3):334-340.

Molitor T W, Bautista E M, Choi C S. 1997. Immunity to Prrsv—Double-Edged Sword. Veterinary Microbiology 55(1-4):265-276.

Murtaugh M P, Elam M R, Kakach L T. 1995. Comparison of the Structural Protein Coding Sequences of the Vr-2332 and Lelystad Virus Strains of the Prrs Virus. Archives of Virology 140(8):1451-1460.

Nath D, van der Merwe P A, Kelm S, Bradfield P, Crocker P R. 1995. The amino-terminal immunoglobulin-like domain of sialoadhesin contains the sialic acid binding site. Comparison with CD22. J Biol Chem 270(44): 26184-26191.

Nauwynck H J, Duan X, Favoreel H W, Van Oostveldt P, Pensaert M B. 1999. Entry of porcine reproductive and respiratory syndrome virus into porcine alveolar macrophages via receptor-mediated endocytosis. Journal of General Virology 80(Part 2):297-305.

Nelsen C J, Murtaugh M P, Faaberg K S. 1999. Porcine reproductive and respiratory syndrome virus comparison: Divergent evolution on two continents. Journal of Virology 73(1):270-280.

Nielsen H S, Liu G, Nielsen J, Oleksiewicz M B, Botner A, Storgaard T, Faaberg K S. 2003. Generation of an infectious clone of VR-2332, a highly virulent North American type isolate of porcine reproductive and respiratory syndrome virus. Journal of Virology 77(6):3702-3711.

Nielsen M J, Madsen M, Moller H J, Moestrup S K. 2006. The macrophage scavenger receptor CD163: endocytic properties of cytoplasmic tail variants. J Leukoc Biol 79(4):837-845.

Oetke C, Vinson M C, Jones C, Crocker P R. 2006. Sialoadhesin-deficient mice exhibit subtle changes in B- and T-cell populations and reduced immunoglobulin M levels. Mol Cell Biol 26(4):1549-1557.

Plagemann P G W. 1996. Lactate dehydrogenase-elevating virus and related viruses. In Fields Virology, 3rd Ed, Fields, B et al, ed:1105-1120.

Ritter M, Buechler C, Langmann T, Orso E, Klucken J, Schmitz G. 1999a. The scavenger receptor CD163: regulation, promoter structure and genomic organization. Pathobiology 67(5-6):257-261.

Ritter M, Buechler C, Langmann T, Schmitz G. 1999b. Genomic organization and chromosomal localization of the human CD163 (M130) gene: a member of the scavenger receptor cysteine-rich superfamily. Biochem Biophys Res Commun 260(2):466-474.

Ropp S L, Wees C E M, Fang Y, Nelson E A, Rossow K D, Bien M, Arndt B, Preszler S, Steen P, Christopher-Hennings J, Collins J E, Benfield D A, Faaberg K S. 2004. Characterization of emerging European-like porcine reproductive and respiratory syndrome virus isolates in the United States. Journal of Virology 78(7):3684-3703.

Rowland R R, Steffen M, Ackerman T, Benfield D A. 1999. The evolution of porcine reproductive and respiratory syndrome virus: quasispecies and emergence of a virus subpopulation during infection of pigs with VR-2332. Virology 259:262-266.

Sanchez-Torres C, Gomez-Puertas P, Gomez-del-Moral M, Alonso F, Escribano J M, Ezquerra A, Dominguez J. 2003. Expression of porcine CD163 on monocytes/macrophages correlates with permissiveness to African swine fever infection. Arch Virol 148(12):2307-2323.

Snijder E J, Meulenberg J J M. 1998. THE MOLECULAR BIOLOGY OF ARTERIVIRUSES [Review]. Journal of General Virology 79(Part 5):961-979.

Suarez P, Diazguerra M, Prieto C, Esteban M, Castro J M, Nieto A, Ortin J. 1996. Open Reading Frame 5 of Porcine Reproductive and Respiratory Syndrome Virus as a Cause of Virus-Induced Apoptosis. Journal of Virology 70(5): 2876-2882.

Sur J H, Cooper V L, Galeota J A, Hesse R A, Doster A R, Osorio F A. 1996. In Vivo Detection of Porcine Reproductive and Respiratory Syndrome Virus Rna by in Situ Hybridization at Different Times Postinfection. Journal of Clinical Microbiology 34(9):2280-2286.

Sur J H, Doster A R, Christian J S, Galeota J A, Wills R W, Zimmerman J J, Osorio F A. 1997. Porcine Reproductive and Respiratory Syndrome Virus Replicates in Testicular Germ Cells, Alters Spermatogenesis, and Induces Germ Cell Death by Apoptosis. Journal of Virology 71(12): 9170-9179.

Van Breedam W, Delputte P L, Van Gorp H, Misinzo G, Vanderheij den N, Duan X, Nauwynck H J. 2010a. Porcine reproductive and respiratory syndrome virus entry into the porcine macrophage. J Gen Virol 91(Pt 7):1659-1667.

Van Breedam W, Van Gorp H, Zhang J Q, Crocker P R, Delputte P L, Nauwynck H J. 2010b. The M/GP(5) glycoprotein complex of porcine reproductive and respiratory syndrome virus binds the sialoadhesin receptor in a sialic acid-dependent manner. PLoS Pathog 6(1): e1000730.

van den Hoff M J, Moorman A F, Lamers W H. 1992. Electroporation in 'intracellular' buffer increases cell survival. Nucleic Acids Res 20(11):2902.

Van Gorp H, Delputte P L, Nauwynck H J. 2010a. Scavenger receptor CD163, a Jack-of-all-trades and potential target for cell-directed therapy. Mol Immunol 47(7-8):1650-1660.

Van Gorp H, Van Breedam W, Delputte P L, Nauwynck H J. 2008. Sialoadhesin and CD163 join forces during entry of the porcine reproductive and respiratory syndrome virus. J Gen Virol 89(Pt 12):2943-2953.

Van Gorp H, Van Breedam W, Van Doorsselaere J, Delputte P L, Nauwynck H J. 2010b. Identification of the CD163 protein domains involved in infection of the porcine reproductive and respiratory syndrome virus. J Virol 84(6):3101-3105.

Vanderheij den N, Delputte P L, Favoreel H W, Vandekerckhove J, Van Damme J, van Woensel P A, Nauwynck H J. 2003. Involvement of sialoadhesin in entry of porcine reproductive and respiratory syndrome virus into porcine alveolar macrophages. Journal of Virology 77(15):8207-8215.

Vinson M, Vandermerwe P A, Kelm S, May A, Jones E Y, Crocker P R. 1996. Characterization of the Sialic Acid-Binding Site in Sialoadhesin by Site-Directed Mutagenesis. Journal of Biological Chemistry 271(16):9267-9272.

Welch S K W, Calvert J G. 2010. A brief review of CD163 and its role in PRRSV infection. Virus Research 154:98-103.

Wensvoort G, Terpstra C, Pol J M A, ter Laak E A, Bloemrad M, de Kluyer E P, Kragten C, van Buiten L, den Besten A, Wagenaar F, Broekhuijsen J M, Moonen P L J M, Zetstra T, de Boer E A, Tibben H J, de Jong M F, van't Veld P, Groenland G J R, van Gennep J A, Voets M T H, Verheijden J H M, Braamskamp J. 1991. Mystery swine disease in The Netherlands: the isolation of Lelystad virus. Veterinary Quarterly 13:121-130.

Wills R W, Zimmerman J J, Yoon K J, McGinley M J, Hill H T, Platt K B, Christopherhennings J, Nelson E A. 1997. Porcine Reproductive and Respiratory Syndrome Virus—a Persistent Infection. Veterinary Microbiology 55(1-4):231-240.

Wissink E H J, van Wijk H A R, Pol J M A, Godeke G J, van Rijn P A, Rottier P J M, Meulenberg J J M. 2003. Identification of porcine alveolar macrophage glycoproteins involved in infection of porcine respiratory and reproductive syndrome virus. Archives of Virology 148 (1):177-187.

Yoon I L, Joo H S, Christianson W E, Morrison R B, Dial G D. 1993. Persistent and contact infection in nursery pigs experimentally infected with PRRS virus. Swine Health and Production 1:5-8.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above products and methods without departing from the scope of the invention, it is intended that all matter contained in the above description and shown in the accompanying drawing[s] shall be interpreted as illustrative and not in a limiting sense.

What is claimed is:

1. A genetically modified swine comprising an alteration in a CD 163 gene sequence, wherein the alteration reduces the expression of CD 163, wherein the alteration is in a non-coding sequence of the CD163 gene, and wherein the swine exhibits increased resistance to porcine reproductive and respiratory syndrome virus (PRRSV).

2. The genetically modified swine of claim 1, wherein the non-coding sequence comprises an intron, a promoter, a 5'-untranslated sequence, or a 3'-untranslated sequence.

3. The genetically modified swine of claim 2, wherein the non-coding sequence comprises a promoter.

4. The genetically modified swine of claim 1, wherein the alteration comprises an insertion, a deletion, a point mutation, or a combination of any thereof.

5. The genetically modified swine of claim 1, wherein the wherein the swine further comprises a mutation in one or both alleles of a SIGLEC1 gene.

6. The genetically modified swine of claim 5, wherein the mutation comprises a partial deletion, a complete deletion, a frame-shift mutation, a nonsense mutation, a missense mutation, a point mutation, or a combination of any thereof.

7. The genetically modified swine of claim 5, wherein the SIGLEC1 allele has been mutated by deletion of part of exon 1 and all of exons 2 and 3.

8. The genetically modified swine of claim 1, wherein the swine does not comprise a mutation in either allele of a SIGLEC1 gene.

9. A genetically modified swine comprising an alteration in a CD 163 gene sequence, wherein the swine exhibits increased resistance to porcine reproductive and respiratory syndrome virus (PRRSV), wherein the alteration reduces the expression of CD163.

10. The genetically modified swine of claim 9, wherein the alteration in the CD163 gene sequence comprises an alteration in a coding region of the CD163 gene sequence.

11. The genetically modified swine of claim 9, wherein the alteration in the CD163 gene sequence comprises an alteration in a non-coding region of the CD163 gene sequence.

12. The genetically modified swine of claim 11, wherein the non-coding sequence comprises an intron, a promoter, a 5'-untranslated sequence, or a 3'-untranslated sequence.

13. The genetically modified swine of claim 12, wherein the non-coding sequence comprises a promoter.

14. The genetically modified swine of claim 9, wherein the alteration comprises an insertion, a deletion, a frame shift mutation, a nonsense mutation, a missense mutation, a point mutation, or a combination thereof.

15. The genetically modified swine of claim 9, wherein the swine further comprises a mutation in one or both alleles of a SIGLEC1 gene.

16. The genetically modified swine of claim 15, wherein the mutation comprises a partial deletion, a complete deletion, a frame-shift mutation, a nonsense mutation, a missense mutation, a point mutation, or a combination of any thereof.

17. The genetically modified swine of claim 15, wherein the SIGLEC1 allele has been mutated by deletion of part of exon 1 and all of exons 2 and 3.

18. The genetically modified swine of claim 9, wherein the swine does not comprise a mutation in either allele of a SIGLEC1 gene.

19. Progeny of the genetically modified swine of claim 9, wherein the progeny comprise the alteration in the CD163 gene sequence.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
ggaacaggct gagccaataa                                              20

<210> SEQ ID NO 2
<211> LENGTH: 17
<212> TYPE: DNA
<213> ORGANISM: Artificial Sequence
<220> FEATURE:
<223> OTHER INFORMATION: Primer

<400> SEQUENCE: 2
gcattcctag gcacagc                                                 17
```

```
<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
ggttctaagt actgtggttt cc                                              22

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
agaggccact tgtgtagcgc                                                 20

<210> SEQ ID NO 5
<211> LENGTH: 17
<212> TYPE: DNA
<213> ORGANISM: Artificial Sequence
<220> FEATURE:
<223> OTHER INFORMATION: Primer

<400> SEQUENCE: 5
ctccttgcca tgtccag                                                    17

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
caggtaccag gaaaaacggg t                                               21

<210> SEQ ID NO 7
<211> LENGTH: 360
<212> TYPE: DNA
<213> ORGANISM: Mus musculus

<400> SEQUENCE: 7
gccagaccac atggggtgtc tccagtccca agaatgtgca gggcttgtcg ggatcctgcc     60
tgctcattcc ctgcatcttc agctaccctg ccgatgtccc agtgtccaat ggcatcacag    120
ccatctggta ctatgactac tcgggcaagc ggcaggtggt aatccactca ggggacccca    180
agctggtgga caagcgtttc agggtcgag ctgaactgat ggggaacatg gaccacaagg     240
tgtgcaacct gttgctcaaa gacttgaagc ctgaagactc tggcacctac aacttccgct    300
ttgagatcag tgatagcaac cgctggttag atgtcaaagg caccacggtc actgtgacaa    360

<210> SEQ ID NO 8
<211> LENGTH: 119
<212> TYPE: PRT
<213> ORGANISM: Mus musculus

<400> SEQUENCE: 8

Gln Thr Thr Trp Gly Val Ser Ser Pro Lys Asn Val Gln Gly Leu Ser
1               5                   10                  15
```

-continued

```
Gly Ser Cys Leu Leu Ile Pro Cys Ile Phe Ser Tyr Pro Ala Asp Val
            20                  25                  30

Pro Val Ser Asn Gly Ile Thr Ala Ile Trp Tyr Tyr Asp Tyr Ser Gly
        35                  40                  45

Lys Arg Gln Val Val Ile His Ser Gly Asp Pro Lys Leu Val Asp Lys
        50                  55                  60

Arg Phe Arg Gly Arg Ala Glu Leu Met Gly Asn Met Asp His Lys Val
65                      70                  75                  80

Cys Asn Leu Leu Leu Lys Asp Leu Lys Pro Glu Asp Ser Gly Thr Tyr
                85                  90                  95

Asn Phe Arg Phe Glu Ile Ser Asp Ser Asn Arg Trp Leu Asp Val Lys
            100                 105                 110

Gly Thr Thr Val Thr Val Thr
        115
```